(12) United States Patent
Tolleson et al.

(10) Patent No.: US 7,674,937 B2
(45) Date of Patent: Mar. 9, 2010

(54) HYDROFORMYLATION CATALYSTS

(75) Inventors: Ginette Struck Tolleson, Longview, TX (US); Thomas Allen Puckette, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 12/128,414

(22) Filed: May 28, 2008

(65) Prior Publication Data

US 2009/0299099 A1   Dec. 3, 2009

(51) Int. Cl.
 *C07C 9/02*   (2006.01)
 *C07C 45/50*   (2006.01)
 *B01J 31/00*   (2006.01)

(52) U.S. Cl. .................. 568/14; 568/451; 568/454; 502/155; 502/166

(58) Field of Classification Search .................. 568/14, 568/451, 454; 502/155, 166
 See application file for complete search history.

(56) References Cited

U.S. PATENT DOCUMENTS

| | | |
|---|---|---|
| 3,239,566 A | 3/1966 | Slaugh |
| 3,527,809 A | 9/1970 | Pruett et al |
| 3,560,539 A | 2/1971 | Booth |
| 4,200,592 A | 4/1980 | Davidson et al. |
| 4,482,749 A | 11/1984 | Dennis et al. |
| 4,496,768 A | 1/1985 | Dennis et al. |
| 4,503,260 A | 3/1985 | Auvil et al. |
| 4,687,866 A | 8/1987 | Oswald et al. |
| 5,059,710 A | 10/1991 | Abatjoglou et al. |
| 5,288,918 A | 2/1994 | Maher et al. |
| 5,756,855 A | 5/1998 | Abatjoglou et al. |
| 5,840,647 A | 11/1998 | Puckette et al. |
| 6,130,358 A | 10/2000 | Tolleson et al. |
| 6,515,161 B1 | 2/2003 | Kreutzer et al. |
| 6,693,219 B2 | 2/2004 | Puckette et al. |
| 6,831,035 B2 | 12/2004 | Puckette et al. |
| 6,846,960 B2 | 1/2005 | Tolleson et al. |
| 6,906,225 B2 | 6/2005 | Puckette et al. |
| 6,995,292 B2 | 2/2006 | Tolleson et al. |
| 2008/0154067 A1 | 6/2008 | Liu et al. |

FOREIGN PATENT DOCUMENTS

| | | |
|---|---|---|
| JP | 57-118527 A | 7/1982 |
| WO | WO 01/51441 A1 | 7/2001 |
| WO | WO 2005-058788 | 6/2005 |
| WO | WO 2006/003431 A1 | 1/2006 |

OTHER PUBLICATIONS

Deerenburg et al. Chiral Phosphine-Phosphite Ligands in the Highly Enantioselective Rhodium-Catalyzed Asymmetric Hydrogenation. Journal of Organic Chemistry, 2001, vol. 66, p. 7626-7631.*
Vargas et al. Iridium Complexes with Phosphine-Phosphite Ligands. Organometallics, 2006, vol. 25, p. 961-973.*
Rubio et al. Asymmetric Hydroformylation of Olefins with Rh Catalysts Modified with Chiral Phosphine-Phosphite Ligands. Organometallics, 2007, vol. 26, p. 6428-6436.*
Deerenberg et al *Organometallics* 2000, 19, pp. 2065-2072.
Deerenberg et al *J. Org. Chem.* 2000, 65, pp. 4810-4817.
Dieguez et al *Tetrahedron:Asymmetry* 2000, 11, pp. 3161-3166.
Nozaki *The Chemical Record* 2005, 5, pp. 576-584.

* cited by examiner

*Primary Examiner*—Sikarl A Witherspoon
(74) *Attorney, Agent, or Firm*—Eric D. Middlemas; Bernard J. Graves, Jr.

(57) ABSTRACT

This invention is directed to a class of compounds that can be both monodentate and bidentate in their association with a transition metal to form a catalyst for reactions such as the hydroformylation of olefins to produce aldehydes. The compounds contain two phosphorus atoms having different steric and/or electronic nature. In hydroformylation catalysts, the compounds advantageously can produce a variable n/iso product mixture of aldehyde products that can be varied by simply changing process variables such as $[H_2]/[CO]$ partial pressure gas ratio or temperature/inert gas partial pressure.

39 Claims, No Drawings

HYDROFORMYLATION CATALYSTS

FIELD OF THE INVENTION

This invention generally relates to a novel class of compounds containing two phosphorus atoms. The compounds can be both monodentate and bidendate in their association with a transition metal. The invention also generally relates to their use with transition metals to form catalysts, particularly for hydroformylation reactions. The invention also generally relates to processes for the hydroformylation of olefins using such catalysts to provide aldehydes.

BACKGROUND OF THE INVENTION

The hydroformylation reaction is useful in the preparation of aldehyde products by the reaction of one mole of olefin with one mole each of hydrogen and carbon monoxide. The reaction has been especially useful in the preparation of normal and iso-butyraldehyde from propylene. These materials, in turn, are converted into many commercially significant chemical products such as, for example, n-butanol, 2-ethyl-hexanol, n-butyric acid, iso-butanol, neo-pentyl glycol and the like. These products alone represent a multi-billion dollar market worldwide. Additionally, the hydroformylation of alpha-olefins such as 1-octene, 1-hexene and 1-decene yield aldehyde products that are useful feedstocks for the preparation of detergent alcohols. The linear carbon-chain alcohol products are particularly desirable for use in detergent grade products. The hydroformylation of allyl alcohol is used commercially as a route to 1,4-butanediol. In this use of the hydroformylation reaction, it is desirable to obtain aldehyde products where the formyl group is added to the terminal position of the olefin thus obtaining linear carbon-chain aldehyde products.

U.S. Pat. No. 3,527,809 discloses a low pressure and low temperature process that utilizes rhodium catalysts. Since this disclosure, numerous improvements have been made to increase both the activity and the product ratio with a heavy emphasis on yielding linear aldehyde product. However, there is a substantial potential market for derivatives of branched-chain aldehydes, as well as the existing large market for linear aldehyde hydroformylation products.

One disadvantage of known hydroformylation catalysts is that they produce aldehydes with a narrow linear-to-branched (or normal-to-iso) product ratio, regardless of the process conditions employed. Thus, there is a need for catalysts that can yield different n/iso product ratios on demand in a single reactor in order to reduce capital costs, increase the degree of utilization of capital equipment, and more efficiently use reactant feed gases.

Surprisingly, we have found a class of compounds that allows us to widely vary the ratio of butyraldehyde products by varying process conditions such as the hydrogen and carbon monoxide partial pressures, temperature, or inert gas partial pressure.

SUMMARY OF THE INVENTION

In one aspect, this invention provides a compound having one of the following structures (I)-(XVI):

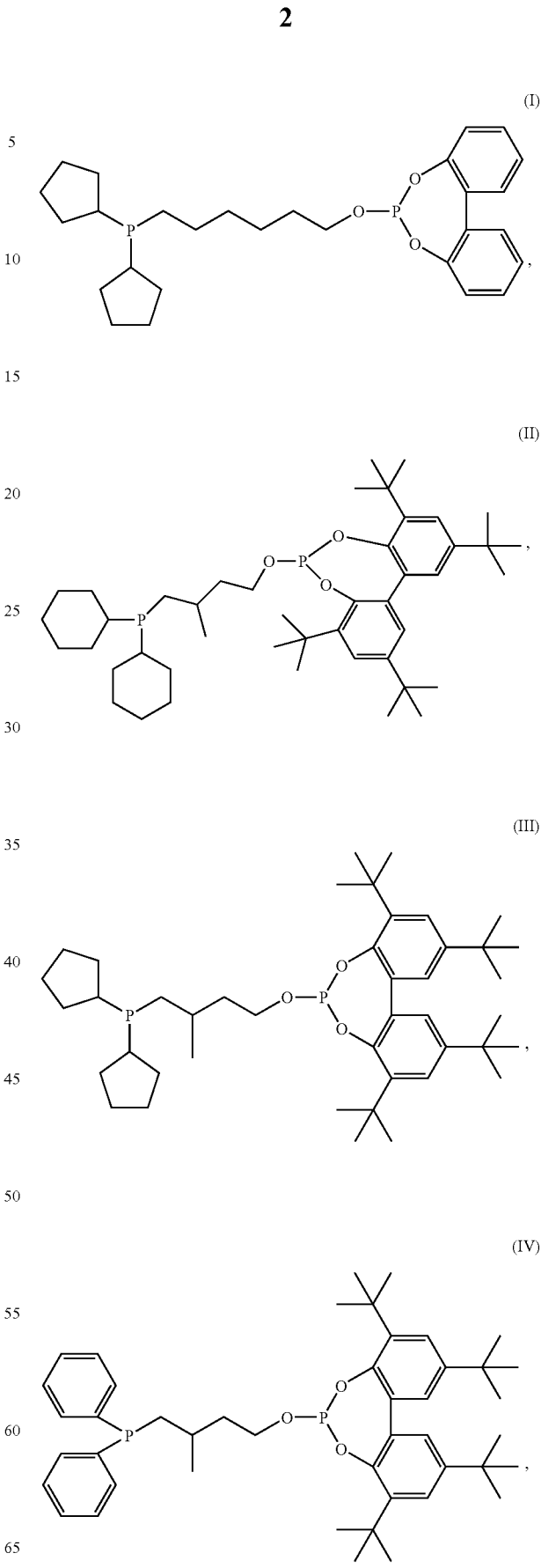

-continued (V)

(VI)

(VII)

(VIII)

(IX)

(X)

(XI)

(XII)

(XIII)

(XIV)

-continued (XV)

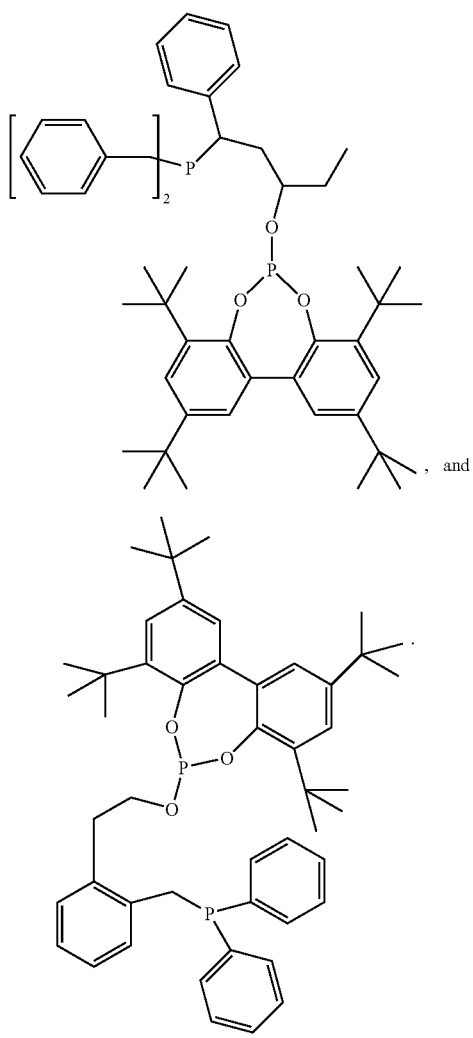

, and (XVI)

In another aspect, the invention provides a catalyst system that comprises (A) at least one transition metal selected from rhenium and Group VIII metals, and (B) at least one ligand selected from structures (I)-(XVI).

In another aspect, the invention provides a process for preparing aldehydes comprising contacting at least one olefin with hydrogen and carbon monoxide in the presence of a catalyst solution comprising (A) rhodium, (B) at least one ligand select from structures (I)-(XVI), and (C) a hydroformylation solvent.

In another aspect, the invention provides a method for changing the normal-to-iso product ratio of a process for preparing aldehydes. The method comprises (a) contacting an olefin with hydrogen and carbon monoxide, at a first hydrogen-to-carbon monoxide partial pressure ratio, in the presence of a catalyst solution comprising (A) rhodium, (B) at least one ligand select from structures (I)-(XVI), and (C) a hydroformylation solvent, to produce aldehydes having a first normal-to-iso product ratio; and (b) contacting said olefin with hydrogen and carbon monoxide, at a second hydrogen-to-carbon monoxide partial pressure ratio which is different from the first hydrogen-to-carbon monoxide partial pressure ratio, in the presence of said catalyst solution to produce aldehydes having a second normal-to-iso product ratio which is different from the first normal-to-iso product ratio.

DETAILED DESCRIPTION OF THE INVENTION

In a first aspect, the invention relates to compounds having the structures of formulas (I)-(XVI) below.

(I)

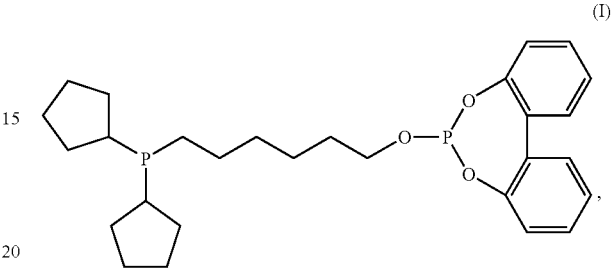

(II)

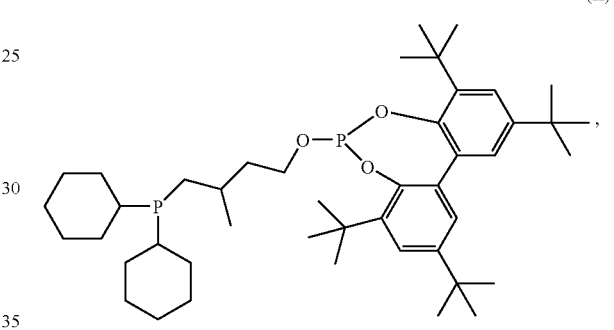

(III)

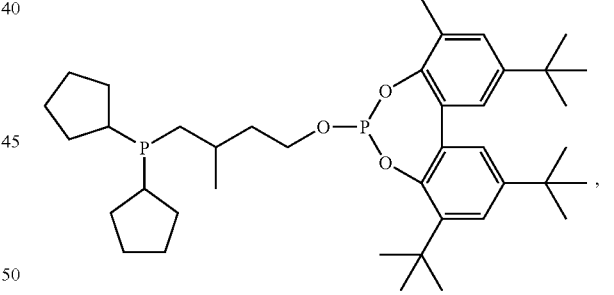

(IV)

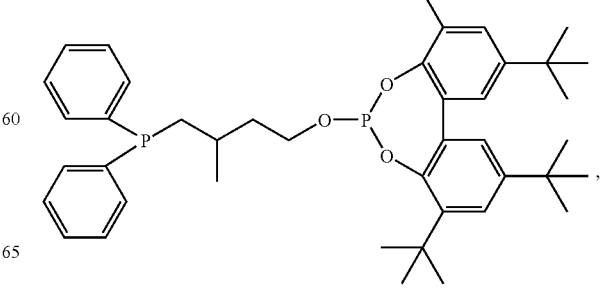

-continued
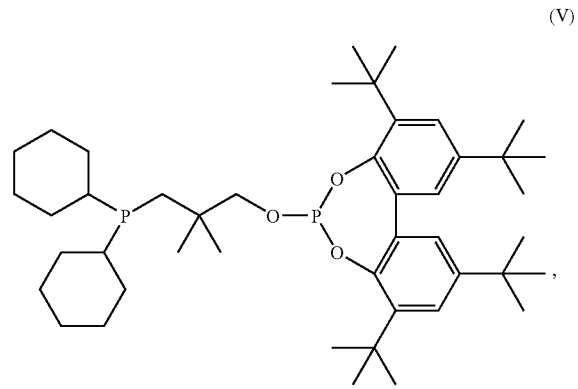
(V)
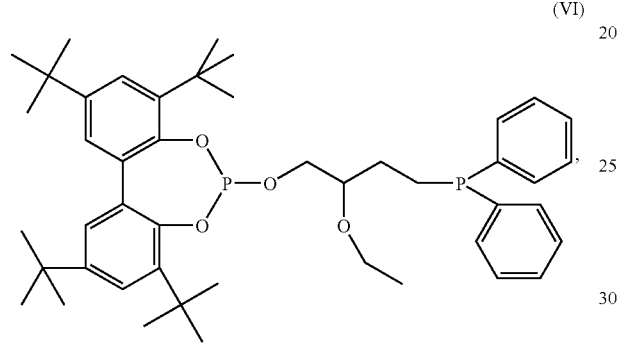
(VI)
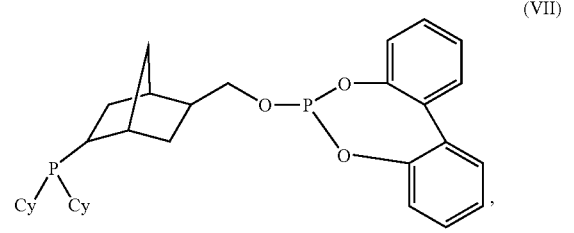
(VII)
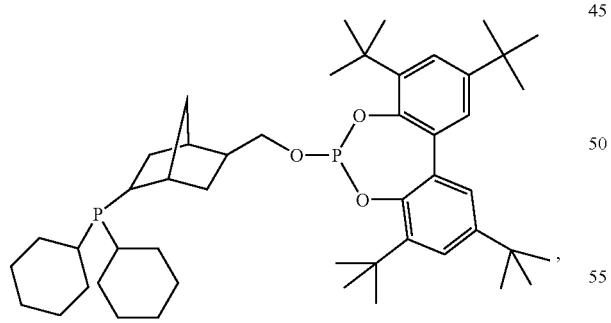
(VIII)
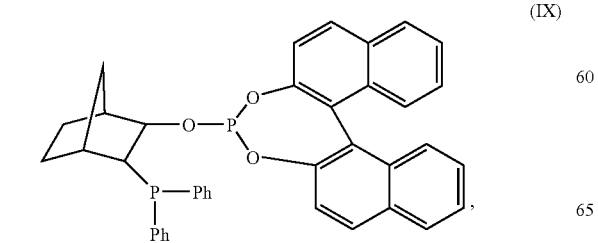
(IX)
-continued
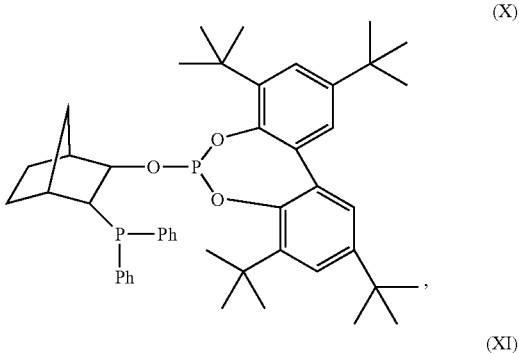
(X)
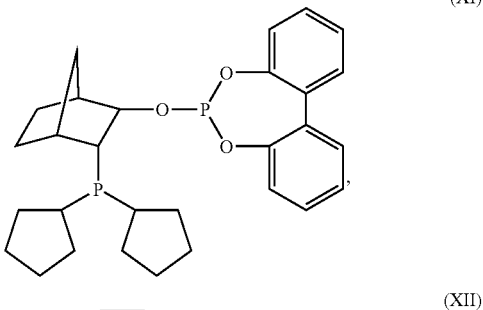
(XI)
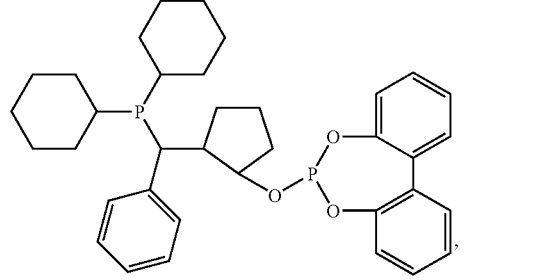
(XII)
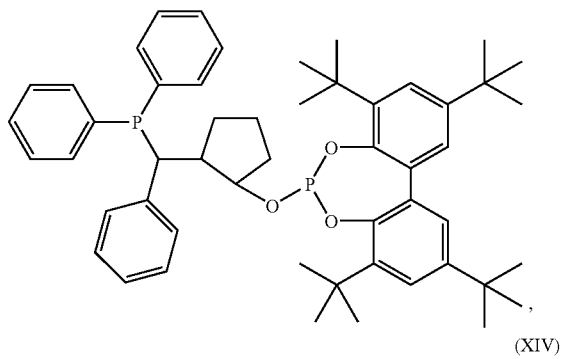
(XIII)
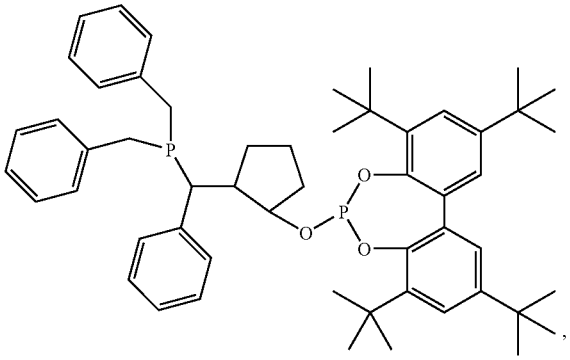
(XIV)

-continued

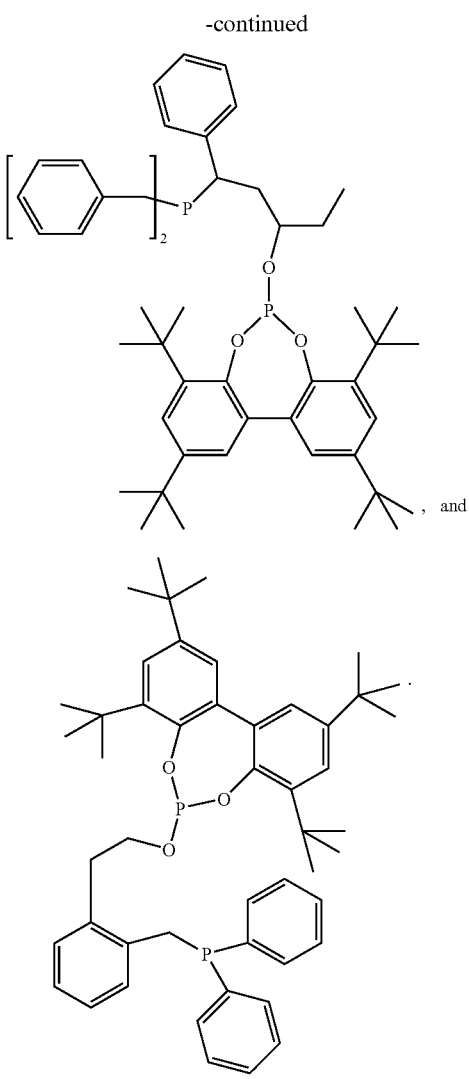

(XV)

(XVI)

These compounds contain phosphorus centers that have significantly different physical properties in terms of ligand basicity, steric bulk, or electron back donation capability. Ligand basicity is defined in a paper by Streuli (*Analytical Chemistry*, 32, 985 (1960)) and steric considerations or cone angle are explained in a paper by Tolman (*J. Am. Chem. Soc.*, 92, 2956 (1970)). The electron donor-acceptor properties of phosphorus ligands can be determined by the method described in an additional paper by Tolman (*J. Am. Chem. Soc.*, 92, 2953 (1970)).

These compounds may be made using the methods discussed in the Examples section.

These compounds are particularly useful as ligands when combined with a transition metal selected from rhenium and Group VIII metals of the Periodic Table of Elements, to form catalyst systems. The novel catalyst systems may be used in a wide variety of transition metal-catalyzed processes such as, for example, hydroformylation, hydrogenation, isomerization, hydrocyanation, hydrosilation, carbonylations, oxidations, acetoxylations, epoxidations, hydroamination, dihydroxylation, cyclopropanation, telomerizations, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. The catalyst systems comprising rhodium as the transition metal are especially useful for the hydroformylation of olefins to produce aldehydes and, therefore, are preferred.

Thus, in a second aspect, the present invention provides a catalyst system comprising (A) at least one transition metal selected from rhenium and Group VIII metals and (B) at least one ligand selected from compounds (I)-(XVI). The transition metal may be provided in the form of various metal compounds such as carboxylate salts of the transition metal.

Many sources of rhodium can be used as the rhodium component for preparation of the preferred catalyst of the invention, provided that the source of rhodium employed can be converted into soluble carbonyl-ligand complexes of rhodium. Suitable rhodium compounds include:

Rhodium (I) dicarbonylacetonylacetonate;
Rhodium (II) octanoate;
Rhodium (II) 2-ethylhexanoate;
Rhodium (II) acetate;
Rhodium (0) carbonyls (e.g. $Rh_6(CO)_{16}$, $Rh_4(CO)_{12}$); and $HRh(CO)(Ph_3P)_3$, as well as mixtures of any two or more thereof.

It is preferred that non-halogen containing rhodium compounds be used to avoid problems of low catalyst activity caused by the presence of residual halide, to avoid the corrosive effects of residual halide ions, and the like. In addition, salts of strong mineral acids are desirably avoided as sources of rhodium because these compounds can decrease catalyst activity under hydroformylation conditions.

We have found rhodium 2-ethylhexanoate to be a particularly preferred source of rhodium from which to prepare the complex catalyst of the invention because it is a convenient source of soluble rhodium, as it can be efficiently prepared from inorganic rhodium salts such as rhodium halides.

In a third aspect, the present invention provides a process for preparing aldehydes which comprises contacting at least one olefin with hydrogen and carbon monoxide in the presence of a catalyst solution comprising (A) rhodium, (B) at least one ligand having the structure of formulas (I)-(XVI), and (C) a hydroformylation solvent.

Suitable hydroformylation solvents include those that do not adversely affect the hydroformylation process and that are inert with respect to the catalyst, olefin, hydrogen and carbon monoxide feeds as well as the hydroformylation products. Inert solvents of this nature are well known to those of skill in the art and include such solvents as benzene, xylene, toluene, as well as their substituted derivatives; pentanes, naphtha, kerosene, mineral oils, cyclohexane, cyclopentane, ethers, esters, etheresters, alcohols, acetals, ketones, water, as well as various mixtures thereof. Preferred solvents are those which are sufficiently high boiling to remain, for the most part, in a gas sparged reactor, and include such compounds as 2,2,4-trimethyl-1,3-pentanediol mono-isobutyrate (which is the chemical name of Texanol® ester alcohol sold by Eastman Chemical Company), and its isomers, 2,2,4-trimethyl-1,3-pentanediol di-isobutyrate, dioctylphthalate, hydrogenated polydecenes (Durasyn 170® and Durasyn 180®; products of Amoco Chemicals), as well as the by-products of the hydroformylation reaction, such as alcohols, esters, acetals and hydroxyaldehydes which are retained as high boiling liquids at the bottom of subsequent distillation columns. Preferred solvents and solvent combinations for less volatile and non-volatile aldehyde products include 1-methyl-2-pyrrolidinone, dimethylformamide, perfluorinated solvents such as perfluorokerosene, sulfolane, water, and high boiling hydrocarbon liquids as well as combinations of these solvents.

The process of the present invention can be carried out with widely varied amounts of rhodium. For example, amounts of catalyst containing as little as about $1\times10^{-6}$ moles of rhodium (calculated based on rhodium metal) per mole of olefin in the reactor zone can be employed. Such low catalyst concentrations are not generally commercially desirable since the reaction rates are frequently rather low. There is no upper limit as to operable catalyst concentrations, but such upper limit is generally determined by the high cost of rhodium metal and the fact that no advantage is generally obtained with catalyst amounts greater than about $1\times10^{-1}$ moles of rhodium per mole of olefin in the reactor zone. Concentrations in the range of about $1\times10^{-5}$ to about $5\times10^{-2}$ moles of rhodium per mole of olefin are preferred. Rhodium concentrations in the range of about $1\times10^{-4}$ up to $1\times10^{-3}$ are most preferred because most efficient utilization of rhodium is obtained while the cost of the rhodium component is maintained within a commercially reasonable amount.

The molar ratios of ligand to rhodium can vary over a wide range. Typically, the ligand to rhodium ratio will vary within the range of about 1 up to 50. Preferably, the molar ratio of ligand to rhodium will vary within the range of 2 up to 30. In a most preferred embodiment, the molar ratio of ligand to rhodium will vary within the range of about 3 up to 20.

No special provisions are required for the preparation of the catalyst employed in the practice of the present invention, although it is preferred, for high catalyst activity, that all manipulations of the rhodium and phosphorus components be carried out under an inert atmosphere, e.g., $N_2$, Ar, and the like. The desired quantities of a suitable rhodium compound and ligand can be charged to the reactor in a suitable solvent. The sequence in which the various catalyst components are charged to the reactor is not critical.

Olefins contemplated for use in the practice of the present invention include straight chain, branched chain, or cyclic, terminal or internal mono-olefins containing in the range of 2 up to 20 carbon atoms and non-conjugated polyolefins typically having in the range of 5 up to 5,000 carbon atoms, e.g., polybutadiene, with each of the above optionally containing groups or substituents which do not interfere with the hydroformylation process. Such substituents that do not interfere with the hydroformylation process include ethers, esters, amides, acetals, ketals, tertiary amines, ketones, aldehydes, nitriles and alcohols. Substituted olefins may include allyl alcohol, allyl acetate, 4-hydroxy-1-butene, and the like. Branched olefins such as isobutene and cis-2-butene may be used as feedstock for the preparation of aldehyde products. Diolefins such as 1,7-octadiene and the like may also be used to prepare dialdehyde products provided that the two carbon-carbon double bonds are not in conjugation. Particularly desirable olefins for use in the process of the invention include without limitation propylene, isobutene, cis-2-butene, 1-hexene, 1-octene, 1-decene, allyl alcohol, allyl acetate, 4-hydroxy-1-butene, and 1,7-octadiene.

Many possible variations exist for the hydroformylation reaction process presented in this invention. For example, the process can be carried out in a gas sparged reactor such that the catalyst which is dissolved in a high boiling organic solvent under pressure does not leave the reaction zone with the aldehyde product which is taken overhead by the unreacted gases. The overhead gases are then chilled in a vapor liquid separator to condense out the aldehyde product, the gases being recycled to the reactor and the liquid product let down to atmospheric pressure for separation and purification by conventional technique. The process may also be practiced in a batchwise manner by contacting the olefin, hydrogen and carbon monoxide with the present catalyst in an autoclave. High boiling aldehyde products such as nonyl aldehydes may be prepared in a continuous manner with the aldehyde product being removed from the reactor zone as a liquid in combination with the catalyst. The aldehyde product may be separated from the catalyst by conventional means such as by distillation and the catalyst then recycled back to the reactor. It will be apparent to those skilled in the art that other reactor schemes may be used with this invention.

The present invention can be operated within the regime of ambient pressure to elevated pressure of 882 psig (6081 kPa) with the preferred range being between 90 and 450 psig pressure (621-3103 kPa). Lower pressures do not adversely effect the catalyst, but it may lead to an overall reduction in reaction rate. The hydroformylation process of this invention is preferably carried out at about 50 psig to 800 psig (345-5516 kPa) with from about 100 to 400 psig (690-2758 kPa) being preferred. The pressure limitations on the present invention are set on the lower end by the need for effective mass transfer and limited on the upper extreme by the high cost of compression.

This process is effective over a wide range of reaction temperatures. The reaction temperature can be varied from about 20° C. to 200° C., but preferably from about 50° C. to 150° C. and most preferably from about 80° C. to about 130° C. Temperatures above 200° C. may rapidly deactivate the catalyst. Temperatures below the preferred range will not adversely affect the catalyst, but the rate of reaction may be substantially reduced.

In the present invention, a syn gas containing hydrogen and carbon monoxide can be introduced into the reactor in a continuous manner by means, for example, of a compressor. The partial pressure ratio of the hydrogen to carbon monoxide in the feed can be selected according to the desired linear to branched isomer ratio in the product. Generally, the partial pressure of hydrogen in the reactor is maintained within the range of about 20 to 200 psia (138-1380 kPa). The partial pressure of carbon monoxide in the reactor is maintained within the range of about 20 to 200 psia (138-1380 kPa). The ratio of hydrogen to carbon monoxide can be varied widely within these partial pressure ranges for the hydrogen and carbon monoxide. The ratio of the hydrogen to carbon monoxide and the partial pressure of each in the syn gas can be readily changed by the addition of either hydrogen or carbon monoxide to the syn gas stream.

Surprisingly, we have found that with the phosphorus ligands disclosed in this invention, the ratio of linear to branched products can be varied widely by changing the partial pressures of hydrogen and carbon monoxide in the reactor. While not wishing to be bound to theory, we believe, after review of the empirical data, that the catalysts of the invention are particularly effective in the hydroformylation reaction because the two phosphorus centers of the ligand have differing binding affinities for the rhodium atom and are attached to a flexible molecule that will allow the association/disassociation process to occur readily. In the practice of the present invention, this capability is exploited by changing the carbon monoxide partial pressure or temperature of the reaction, which in turn, shifts the equilibrium between mono-ligated rhodium centers and di-ligated rhodium centers in the catalyst. Under higher carbon monoxide partial pressures or higher temperatures, an abundance of mono-ligated rhodium centers exist, and the n/iso ratio in the product aldehyde is lowered as mono-ligated rhodium complexes produce a greater portion of the branched isomer than do di-ligated rhodium species. At lower carbon monoxide partial pressures or lower temperatures, the catalyst equilibrium shifts towards the formation of di-ligated rhodium centers. As a result, the n/i ratio of the product aldehyde shifts upward.

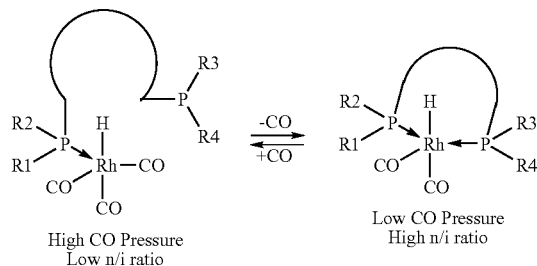

High CO Pressure
Low n/i ratio

Low CO Pressure
High n/i ratio

Thus, in a fourth aspect, the present invention provides a method for changing the normal-to-iso product ratio of a process for preparing aldehydes without the need for changing reactors or catalysts. The method comprises (a) contacting an olefin with hydrogen and carbon monoxide, at a first hydrogen-to carbon monoxide partial pressure ratio, in the presence of a catalyst solution comprising (A) rhodium, (B) at least one ligand select from structures (I)-(XVI), and (C) a hydroformylation solvent, to produce aldehydes having a first normal-to-iso product ratio; and (b) contacting said olefin with hydrogen and carbon monoxide, at a second hydrogen-to-carbon monoxide partial pressure ratio which is different from the first hydrogen-to-carbon monoxide partial pressure ratio, in the presence of said catalyst solution to produce aldehydes having a second normal-to-iso product ratio which is different from the first normal-to-iso product ratio.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

This invention can be further illustrated by the following examples of preferred embodiments thereof, although it will be understood that these examples are included merely for purposes of illustration and are not intended to limit the scope of the invention.

EXAMPLES

Example 1

Preparation of Compound (III)

Dicyclopentylphosphine (5 ml, 27.35 mmoles) was mixed with AIBN (2,2'-azobisisobutyronitrile, 0.6 g) and 3-methyl-3-buten-1-ol (3.53 g, 41 mmoles) under nitrogen and was then heated at 80° C. overnight. Two more portions of 0.5 g of AIBN were added. The mixture was then heated to 120° C. briefly and then cooled to room temperature. The hydroxyphosphine product was then purified by Kugel-Rohr distillation with the product distilling at 120-130° C./0.5 mmHg and yielding 4.93 g of yellow oil.

2,2',4,4'-tetra-tert-butylbiphenylphosphorchlorodite (5.6 g, 0.012 moles) in 50 ml of toluene was reacted with a solution of the hydroxyphosphine (3 g, 0.012 moles) and triethylamine (5 ml, 0.035 moles) in toluene (30 ml) at 0° C. The mixture was stirred overnight at room temperature. The reaction mixture was then filtered, and the solvent was stripped off with nitrogen flow. The residue was redissolved in toluene and purified by passing it through a short column of alumina. The solvent was removed, leaving a light-yellow thick oil. Final overall purified yield was 3.89 g. $^{31}P\{^1H\}$ in ppm: 134.5, −13.44.

Example 2

Preparation of Compound (IX)

Tetrahydrofuran (100 ml) was added to a 500 ml 3-neck round bottom flask under nitrogen. 16 ml of diphenylphosphine was measured out into a syringe under nitrogen and was then added to the flask. The flask was placed into an ice bath. N-butyl lithium (45 ml) was then added slowly by syringe. The reaction was allowed to stir at ice temperature for 1 hour. An addition funnel containing 10 g of exo-2,3-epoxynorbornane dissolved in 45 ml of THF was added to the flask, and the solution was added dropwise. The reaction solution was allowed to gradually come to room temperature, and then it was stirred overnight. The reaction mixture was worked up by pouring carefully into a nitrogen flushed solution of water and diethyl ether (50:50 mixture, ~100 ml). The layers are separated in a nitrogen flushed separatory funnel, the water layers washed with ether, the organic layers combined, and then the solvent was stripped off overnight with a nitrogen flow. The product hydroxyphosphine was purified by distillation by Kugel-Rohr at >180° C. Purified yield was 22 g (81%).

The hydroxyphosphine (5 g) was placed in a 3-neck 500 ml round bottom flask equipped with a Dean-Stark apparatus. 100 ml of toluene was added. The toluene solution was refluxed and ~30 ml of the collected wet toluene was discarded. The flask was cooled to room temperature and the Dean-Stark apparatus was removed. The flask was placed into an ice bath. 6.7 ml of triethylamine was added by syringe to the solution. An addition funnel which contained the binaphthylchlorophosphite (5.92 g) in toluene (~30 ml) was placed on the flask. This solution was added slowly, dropwise, to the solution in the flask below. After the addition was complete, the ice bath was removed, and the reaction was allowed to come to room temperature overnight. It was then worked up by filtering the solution under a nitrogen atmosphere and then stripping off the solvent. The residue was redissolved into toluene and filtered on a short alumina column under a nitrogen atmosphere. The solvent was again stripped off. The resulting yield was 7.15 g (69%). $^{31}P\{^1H\}$ NMR (ppm): 145.0, −15.3.

Example 3

Preparation of Compound (XIV)

The procedure listed above for Compound (IX) was used for the preparation of this compound. Tribenzyl phosphine (12.2 g) was reacted with 25 ml (2M) n-butyl lithium and 3.5 ml of cyclopentene oxide in THF to give 15.1 g of the hydroxyphosphine. The hydroxyphosphine was then reacted with 18.5 g of 2,2',4,4'-tetra-tert-butylbiphenyl-phosphorchlorodite and 16.4 ml of triethylamine to yield 18.46 g of purified product (57.3%). $^{31}P\{^1H\}$ NMR (ppm): 144.4, −8.7.

Example 4

Preparation of Compound (V)

The procedure similar to that listed above for Compound (IX) was used for the preparation of this compound. Dicyclohexylphosphine (4 ml) was reacted with 2,2-dimethyl oxetane (2.06 ml) in the presence of 10 ml of n-butyl lithium (2M) in THF. The resulting hydroxyphosphine (2.84 g of the 5.12 g produced) was reacted with 2,2',4,4'-tetra-tert-butylbiphenylphosphorchlorodite (4.75 g) in the presence of 3.50 ml of triethylamine in THF to yield 5.10 g of product. $^{31}P\{^1H\}$ NMR (ppm): 137.7, −17.9.

General Description of the Hydroformylation Bench Unit Reactor

The reactor is a vertically arranged pipe made of stainless steel of a 1-inch inside diameter and 4 feet in length. The reactor has a filter element mounted into the side, down near the bottom of the reactor for the inlet of gaseous reactants. The reactor is fitted with a thermocouple to measure the temperature of the catalyst in the reactor. The bottom of the reactor has a high pressure tubing connection that is connected to a cross. One of the connections to the cross permits the addition of non-gaseous reactants such as 1-octene or make-up solvent. Another connection leads to the high-pressure connection of a differential pressure (D/P) cell that is used to measure catalyst level in the reactor and the bottom connection is used for draining the catalyst at the end of the run.

The catalyst is charged to and recovered from the reactor by using a small high-pressure sample cylinder. High pressure argon is used to push the catalyst into the reactor, and the reactor pressure is used to return the catalyst to the sample cylinder at the end of the run.

When used for the hydroformylation of propylene, the reactor is operated in a vapor take-off mode of operation. In this mode, the solution containing the catalyst is sparged under pressure with the incoming reactants of propylene, hydrogen, and carbon monoxide as well as any inert feed such as nitrogen. As butyraldehyde is formed in the catalyst solution, it is removed as a vapor in combination with the unreacted reactant gases out the top of the reactor by a side-port. The gases are then chilled in a high pressure separator where the butyraldehyde product is condensed along with some of the unreacted propylene. The uncondensed gases are let down to atmospheric pressure via the pressure control valve. These gases pass through a series of two dry-ice traps where any other aldehyde product is collected. The product from the high pressure separator is combined with that of the traps, and is subsequently weighed and analyzed by standard gas/liquid phase chromatography (GLC) techniques for the net weight and normal/iso ratio of the butyraldehyde product.

The gaseous feeds to the reactor are fed via twin cylinder manifolds and high pressure mass flow controllers. The hydrogen passes through a commercially available "Deoxo" (Registered trademark of Engelhard Inc.) catalyst bed to remove any oxygen contamination and through a mass flow controller. The carbon monoxide passes through a similar "Deoxo" bed heated to 125° C., and an iron carbonyl removal bed (as disclosed in U.S. Pat. No. 4,608,239). Nitrogen can be added to the feed mixture as an inert gas. Nitrogen, when added, is metered, and then mixed with the hydrogen feed prior to the hydrogen "Deoxo" bed. Propylene is fed to the reactor from feed tanks that are pressurized with hydrogen and is controlled using a liquid mass flow meter. All gases and propylene are passed through a preheater to ensure vaporization of the liquid propylene. Any higher boiling liquid olefin feeds such as 1-octene are pumped into the reactor from the bottom cross using a small positive displacement feed pump. A small feed tank also measures the amount of olefin fed in this manner.

Example 5

Hydroformylation of Propylene Using Compound (III) as a Ligand

A catalyst solution was prepared under nitrogen using a charge of 25 milligrams of rhodium charged as Rh dicarbonyl acac (0.0625 g, 0.242 mmole), 0.843 grams (1.21 mmole) of Compound (III), and 190 mL of 2,2,4-trimethyl-1,3-pentanediol monoisobutyrate (Texanol® brand) solvent. This was charged to the sample bomb under a nitrogen blanket and then charged to the reactor under argon positive pressure. The reactor was pressured to 260 psig with hydrogen, carbon monoxide, and nitrogen and heated to 115° C. Propylene feed was then started, and the flows were adjusted to the following values reported in liters/min at standard temperature and pressure (STP): hydrogen=3.7 l/min STP; carbon monoxide=3.7 l/min STP; nitrogen=1.1 l/min STP; and propylene=2.1 l/min STP. This is equivalent to having the following partial pressures in the feed to the reactor reported as psia: hydrogen=96; carbon monoxide=96; nitrogen=29; and propylene=54 psia.

The reaction was carried out under the above flows for five hours. The butyraldehyde production rate for the last four hours of operation averaged 13.4 grams/hour for a catalyst activity of 0.76 pounds butyraldehyde/gram of rhodium-hour (lb HBu/g Rh-hr). The product N/Iso ratio was 2.96/1.

Example 6

Hydroformylation of Propylene Using Compound (III) as a Ligand

A catalyst solution was prepared under nitrogen using a charge of 25 milligrams of rhodium charged as Rh dicarbonyl acac (0.0625 g, 0.242 mmole), 0.843 grams (1.21 mmole) of Compound (III), and 190 mL of Texanol® solvent. This was charged to the sample bomb under a nitrogen blanket and then charged to the reactor under argon positive pressure. The reactor was pressured to 260 psig with hydrogen, carbon monoxide, and nitrogen and heated to 115° C. Propylene feed was then started, and the flows were adjusted to the following values reported as liters/min at standard temperature and pressure (STP): hydrogen=3.8 l/min STP; carbon monoxide=1.9 l/min STP; nitrogen=1.9 l/min STP; and propylene=1.9 l/min STP. This is equivalent to having the following partial pressures in the feed to the reactor reported as psia: hydrogen=110; carbon monoxide=55; nitrogen=56; and propylene=54 psia.

The reaction was carried out under the above flows for five hours. The butyraldehyde production rate for the last four hours of operation averaged 36.5 grams/hour for a catalyst activity of 2.62 pounds butyraldehyde/gram of rhodium-hour (lb HBu/g Rh-hr). The product N/Iso ratio was 3.44/1.

Example 7

Hydroformylation of Propylene Using Compound (XIV) as a Ligand

A catalyst solution was prepared under nitrogen using a charge of 25 milligrams of rhodium charged as Rh dicarbonyl acac (0.0625 g, 0.242 mmole), 1.00 grams (1.21 mmole) of Compound (XIV), and 190 mL of Texanol® solvent. This was charged to the sample bomb cylinder under a nitrogen blanket and then charged to the reactor under argon positive pressure. The reactor was pressured to 260 psig with hydrogen, carbon monoxide, and nitrogen and heated to 115° C. Propylene feed was then started, and the flows were adjusted to the following values reported as liters/min at standard temperature and pressure (STP): hydrogen=3.7 l/min STP; carbon monoxide=3.7 l/min STP; nitrogen=1.1 l/min STP; and propylene=2.1 l/min STP. This is equivalent to having the following partial pressures in the feed to the reactor reported as psia: hydrogen=96; carbon monoxide=96; nitrogen=29; and propylene=54 psia.

The reaction was carried out under the above flows for five hours. The butyraldehyde production rate for the last three hours of operation averaged 46.0 grams/hour for a catalyst activity of 4.65 pounds butyraldehyde/gram of rhodium-hour (lb HBu/g Rh-hr). The product N/Iso ratio was 1.76/1.

Example 8

Hydroformylation of Propylene Using Compound (XIV) as a Ligand

A catalyst solution was prepared under nitrogen using a charge of 25 milligrams of rhodium charged as a Rh dicarbonyl acac (0.0625 g, 0.242 mmole), 1.00 grams (1.21 mmole) of Compound (XIV), and 190 mL of Texanol® solvent. This was charged to the sample bomb under a nitrogen blanket and then charged to the reactor under argon positive pressure. The reactor was pressured to 260 psig with hydrogen, carbon monoxide, and nitrogen and heated to 115° C. Propylene feed was then started and the flows were adjusted to the following values reported as liters/min at standard temperature and pressure (STP): hydrogen=3.8 l/min STP; carbon monoxide=1.9 l/min STP; nitrogen=1.9 l/min STP; and propylene=1.9 l/min STP. This is equivalent to having the following partial pressures in the feed to the reactor reported as psia: hydrogen=110; carbon monoxide=55; nitrogen=56; and propylene=54 psia.

The reaction was carried out under the above flows for five hours. The butyraldehyde production rate for the last three hours of operation averaged 66.1 grams/hour for a catalyst activity of 5.6 pounds butyraldehyde/gram of rhodium-hour (lb HBu/g Rh-hr). The product N/Iso ratio was 2.44/1.

Example 9

Hydroformylation of Propylene Using Compound (IX) as a Ligand

A catalyst solution was prepared under nitrogen using a charge of 25 milligrams of rhodium charged as Rh dicarbonyl acac (0.0625 g, 0.242 mmole), 0.741 grams (1.21 mmole) of Compound (IX), and 190 mL of Texanol® solvent. This was charged to the sample bomb under a nitrogen blanket and then charged to the reactor under argon positive pressure. The reactor was pressured to 260 psig with hydrogen, carbon monoxide, and nitrogen and heated to 115° C. Propylene feed was then started and the flows were adjusted to the following values reported as liters/min at standard temperature and pressure (STP): hydrogen=3.7 l/min STP; carbon monoxide=3.7 l/min STP; nitrogen=1.1 l/min STP; and propylene=2.1 l/min STP. This is equivalent to having the following partial pressures in the feed to the reactor reported as psia: hydrogen=96; carbon monoxide=96; nitrogen=29; and propylene=54 psia.

The reaction was carried out under the above flows for five hours. The butyraldehyde production rate for the last three hours of operation averaged 40.7 grams/hour for a catalyst activity of 3.36 pounds butyraldehyde/gram of rhodium-hour (lb HBu/g Rh-hr). The product N/Iso ratio was 5.07/1.

Example 10

Hydroformylation of Propylene Using Compound (IX) as a Ligand

A catalyst solution was prepared under nitrogen using a charge of 25 milligrams of rhodium charged as Rh dicarbonyl acac (0.0625 g, 0.242 mmole), 0.741 grams (1.21 mmole) of Compound (IX), and 190 mL of Texanol® solvent. This was charged to the sample bomb under a nitrogen blanket and then charged to the reactor under argon positive pressure. The reactor was pressured to 260 psig with hydrogen, carbon monoxide, and nitrogen and heated to 115° C. Propylene feed was then started and the flows were adjusted to the following values reported as liters/min at standard temperature and pressure (STP): hydrogen=3.8 l/min STP; carbon monoxide=1.9 l/min STP; nitrogen=1.9 l/min STP; and propylene=1.9 l/min STP. This is equivalent to having the following partial pressures in the feed to the reactor reported as psia: hydrogen=110; carbon monoxide=55; nitrogen=56; and propylene=54 psia.

The reaction was carried out under the above flows for five hours. The butyraldehyde production rate for the last three hours of operation averaged 31.9 grams/hour for a catalyst activity of 2.62 pounds butyraldehyde/gram of rhodium-hour (lb HBu/g Rh-hr). The product N/Iso ratio was 3.97/1.

Example 11

Hydroformylation of Propylene Using Compound (V) as a Ligand

A catalyst solution was prepared under nitrogen using a charge of 25 milligrams of rhodium charged as Rh dicarbonyl acac (0.0625 g, 0.242 mmole), 0.87 grams (1.21 mmole) of Compound (V), and 190 mL of Texanol® solvent. This was charged to the sample bomb under a nitrogen blanket and then charged to the reactor under argon positive pressure. The reactor was pressured to 260 psig with hydrogen, carbon monoxide, and nitrogen and heated to 115° C. Propylene feed was then started, and the flows were adjusted to the following values reported as liters/min at standard temperature and pressure (STP): hydrogen=3.4 l/min STP; carbon monoxide=3.4 l/min STP; nitrogen=0.9 l/min STP; and propylene=1.0 l/min STP. This is equivalent to having the following partial pressures in the feed to the reactor reported as psia: hydrogen=106; carbon monoxide=106; nitrogen=30; and propylene=33 psia.

The reaction was carried out under the above flows for five hours. The butyraldehyde production rate for the last three hours of operation averaged 27.5 grams/hour for a catalyst activity of 2.15 pounds butyraldehyde/gram of rhodium-hour (lb HBu/g Rh-hr). The product N/Iso ratio was 1.93/1.

Example 12

Hydroformylation of Propylene Using Compound (V) as a Ligand

A catalyst solution was prepared under nitrogen using a charge of 25 milligrams of rhodium charged as Rh dicarbonyl acac (0.0625 g, 0.242 mmole), 0.87 grams (1.21 mmole) of Compound (V), and 190 mL of Texanol® solvent. This was charged to the sample bomb under a nitrogen blanket and then charged to the reactor under argon positive pressure. The reactor was pressured to 260 psig with hydrogen, carbon monoxide, and nitrogen and heated to 115° C. Propylene feed was then started and the flows were adjusted to the following values reported as liters/min at standard temperature and pressure (STP): hydrogen=3.5 l/min STP; carbon monoxide=1.3 l/min STP; nitrogen=3.0 l/min STP; and propylene=1.0 l/min STP. This is equivalent to having the following partial pressures in the feed to the reactor reported as psia: hydrogen=110; carbon monoxide=40; nitrogen=92; and propylene=33 psia.

The reaction was carried out under the above flows for five hours. The butyraldehyde production rate for the last three hours of operation averaged 11.8 grams/hour for a catalyst activity of 0.84 pounds butyraldehyde/gram of rhodium-hour (lb HBu/g Rh-hr). The product N/Iso ratio was 7.52/1.

The results of Examples 5-12 are summarized in Table 1 below.

TABLE 1

| Example No. | Ligand | $H_2/CO$ Partial Pressure Ratio | N/Iso Product Ratio |
|---|---|---|---|
| 5 | III | 1/1 | 2.96/1 |
| 6 | III | 2/1 | 3.44/1 |
| 7 | XIV | 1/1 | 1.76/1 |
| 8 | XIV | 2/1 | 2.44/1 |
| 9 | IX | 1/1 | 5.07/1 |
| 10 | IX | 2/1 | 3.97/1 |
| 11 | V | 1/1 | 1.93/1 |
| 12 | V | 2.75/1 | 7.52/1 |

As seen from the results in Table 1 above, the ligands according to the present invention allow the n/iso aldehyde product ratio to be changed widely (e.g., from about 16% to about 290%) by simply changing the $H_2/CO$ partial pressure ratio in the reaction.

Comparative Example 1

Effect of Varying Hydrogen and Carbon Monoxide Partial Pressures

Table 2 below shows the effect of using different partial pressures of hydrogen and carbon monoxide in the reactor feed on the n/iso isomer product ratio of a catalyst known in the art. The runs shown below used ligand α,α'-bis(diphenylphosphino)-o-xylene (from U.S. Pat. No. 4,960,949, Table 1, column 10) in a catalyst charge comprised of 0.0625 gram of rhodium (as rhodium 2-ethylhexanoate) and 1.44 grams of ligand dissolved in 0.195 liter of Texanol® solvent. The experimental conditions were as follows: $N_2$ flow rate: 0.96 liters/min; total reaction pressure: 260 psig; and reaction temperature: 115° C. The reactor was operated for 6 hours under the conditions set forth above.

TABLE 2

Effect of Hydrogen/Carbon Monoxide Ratio on N/Iso Ratio at 115° C. with Rh/α,α'-bis-(diphenylphosphino)-o-xylene Catalyst

| $H_2$ Partial Pressure (psia) | CO Partial Pressure (psia) | $C_3H_6$ Partial Pressure (psia) | N/Iso Product Ratio | Intrinsic Activity (lb HBu/g Rh-hr) |
|---|---|---|---|---|
| 161 | 31 | 55 | 2.38/1 | 3.42 |
| 146 | 49 | 52 | 2.44/1 | 1.91 |
| 96 | 96 | 54 | 2.64/1 | 1.51 |
| 79 | 113 | 56 | 2.85/1 | 1.04 |

The results set forth in Table 2 demonstrate that the normal/iso ratio for aldehyde products was changed by a small extent (~10%) by varying the $H_2/CO$ ratio from 1:1 to 3:1.

Shown below in Table 3 are the results using a flex ratio ligand (XIV) of this invention under some of the same reactor conditions.

TABLE 3

Effect of Hydrogen/Carbon Monoxide Ratio on N/Iso Ratio at 115° C. with Rh/Ligand (XIV) Catalyst

| $H_2$ Partial Pressure in Feed (psia) | Co Partial Pressure in Feed (psia) | N/Iso Product Ratio | Intrinsic Activity (lb HBu/g Rh-hr) |
|---|---|---|---|
| 110 | 40 | 3.22/1 | 10.23 |
| 110 | 55 | 2.45/1 | 5.89 |
| 96 | 96 | 1.76/1 | 4.69 |

From Table 3, it can be seen that the catalyst system of the present invention can provide a greater difference in the n/iso product ratio as the $H_2/CO$ partial pressure ratio was changed from 1:1 to 2:75:1, compared to the catalyst of U.S. Pat. No. 4,960,949. Additionally, the catalyst system of the present invention has a higher activity at a given CO partial pressure than the catalyst of the '949 patent.

Example 13

Preparation of Compound (I)

The compound having structure (I) as set forth herein can be prepared by following the general procedures and conditions employed in Example 1, using dicyclopentylphosphine, 5-hexen-1-ol, and biphenylphosphorchlorodite as starting materials.

Example 14

Preparation of Compound (II)

The compound having structure (II) as set forth herein can be prepared by following the general procedures and conditions employed in Example 1, using dicyclohexylphosphine; 3-methyl-3-buten-1-ol; and 2,2',4,4'-tetra-tert-butylbiphenylphosphorchlorodite as starting materials.

Example 15

Preparation of Compound (IV)

The compound having structure (IV) as set forth herein can be prepared by following the general procedures and conditions employed in Example 1, using diphenylphosphine; 3-methyl-3-buten-1-ol; and 2,2',4,4'-tetra-tert-butylbiphenylphosphorchlorodite as starting materials.

Example 16

Preparation of Compound (VI)

The compound having structure (VI) as set forth herein can be prepared by following the general procedures and conditions employed in Example 1, using diphenylphosphine; 2-ethoxy-3-buten-1-ol; and 2,2',4,4'-tetra-tert-butylbiphenylphosphorchlorodite as starting materials.

Example 17

Preparation of Compound (VII)

The compound having structure (VII) as set forth herein can be prepared by following the general procedures and conditions employed in Example 1, using dicyclohexylphosphine; 5-norbonene-2-methanol; and biphenylphosphorchlorodite as starting materials.

Example 18

Preparation of Compound (VIII)

The compound having structure (VIII) as set forth herein can be prepared by following the general procedures and conditions employed in Example 1, using dicyclohexylphosphine; 5-norbornene-2-methanol; and 2,2',4,4'-tetra-tert-butylbiphenylphosphorchlorodite as starting materials.

Example 19

Preparation of Compound (X)

The compound having structure (X) as set forth herein can be prepared by following the general procedures and conditions employed in Example 2, using diphenylphosphine; exo-2,3-epoxynorbornane; and 2,2',4,4'-tetra-tert-butylbiphenylphosphorchlorodite as starting materials.

Example 20

Preparation of Compound (XI)

The compound having structure (XI) as set forth herein can be prepared by following the general procedures and conditions employed in Example 2, using dicyclopentylphosphine; exo-2,3-epoxynorbornane; and biphenylphosphorchlorodite as starting materials.

Example 21

Preparation of Compound (XII)

The compound having structure (XII) as set forth herein can be prepared by following the general procedures and conditions employed in Example 3, using dicyclohexylbenzylphosphine; cyclopentene oxide; and biphenylphosphorchlorodite as starting materials.

Example 22

Preparation of Compound (XIII)

The compound having structure (XIII) as set forth herein can be prepared by following the general procedures and conditions employed in Example 3, using diphenylbenzylphosphine; cyclopentene oxide; and 2,2',4,4'-tetra-tert-butylbiphenylphosphorchlorodite as starting materials.

Example 23

Preparation of Compound (XV)

Tribenzylphosphine (5 g) was placed into a 250 ml three-neck round bottom flask under nitrogen. About 60 ml of tetrahydrofuran was added by syringe. The flask was cooled with an ice bath and 8.2 ml of n-butyllithium was added slowly by syringe. After stirring for 15 minutes, an addition funnel was attached and epoxybutane (1.42 g) and tetrahydrofuran were added dropwise slowly to the mixture. The reaction was allowed to come to room temperature and stirred overnight. The reaction was worked up by pouring into diethyl ether and water. The organic layer was separated and dried over magnesium sulfate. The hydroxyphosphine product was then filtered and the solvent was removed.

Compound (XV) was then prepared from the hydroxyphosphine product (4.9 g) described above and 2,2',4,4'-tetra-tert-butylbiphenylphosphorchlorodite (6.65 g) following the procedures of the second paragraph of Example 1.

Example 24

Preparation of Compound (XVI)

Under nitrogen, magnesium (1.87 g) was placed in a 3-neck 250 ml round bottom flask along with about 60 ml of diethyl ether and a few crystals of iodine and a few drops of n-butyl lithium (2M). 1-bromo-2-(bromomethyl)benzene (17.5 g) was added to an addition funnel along with 20 ml of diethyl ether. This solution was added dropwise to the mixture. The reaction was refluxed for an additional ½ hour after dropwise addition was completed. Chlorodiphenylphosphine (11.3 ml) in 20 ml of diethyl ether was then added dropwise with vigorous stirring to the Grignard solution at a rate to maintain a reflux. When the addition was complete, the reaction was refluxed for an additional hour and then cooled to room temperature and quenched with aqueous hydrochloric acid (dropwise addition) under nitrogen. The layers were separated and the organic layer was washed with water. The mixture was then filtered, separated, and dried. The solvent was then removed to obtain 24.8 g of (2-bromobenzyl)diphenyl-phosphine.

Under nitrogen, magnesium (1.0 g) was placed in a 3-neck 500 ml round bottom flask along with about 100 ml of tetrahydrofuran. Tetrahydrofuran (30 ml) and 0.2 ml of dibromoethane were placed in an addition funnel and added dropwise to the solution. The mixture was then refluxed. After cooling to room temperature, (2-bromobenzyl)diphenylphosphine (10 g) was added to the funnel along with 40 ml of tetrahydrofuran. Dibromoethane (0.15 ml) and iodine (small amount as initiator) were also added to the funnel. This solution was added slowly to the mixture. The cloudy mixture was refluxed for three hours.

The orange solution was cooled slightly and cannulated into another nitrogen flushed 3-neck round bottom flask equipped with a condenser and containing 1,3-dioxolan-2-one (2.47 g in THF). The reaction became yellow-green and was refluxed for 2 hours. After cooling to room temperature and stirring overnight, the solution was poured into nitrogen flushed sulfuric acid in an ice-cooled flask. The aqueous layer was washed with diethyl ether and the combined organics were washed with water and dried over magnesium sulfate. 2-(2-((diphenylphosphino)methyl)phenyl)ethanol (7.2 g) was isolated by filtering and evaporating off the solvent with nitrogen flow.

Compound (XVI) was then prepared from the 2-(2-((diphenylphosphino)methyl)phenyl)ethanol (5 g) described above and 2,2',4,4'-tetra-tert-butylbiphenylphosphorchlorodite (8.15 g) following the procedures of the second paragraph of Example 1.

The invention has been described in detail with particular reference to preferred embodiments thereof, but it will be understood that variations and modifications can be effected within the spirit and scope of the invention.

We claim:

1. A compound having one of the following structures:

(I)

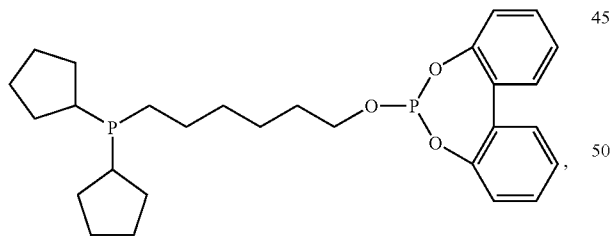

(II)

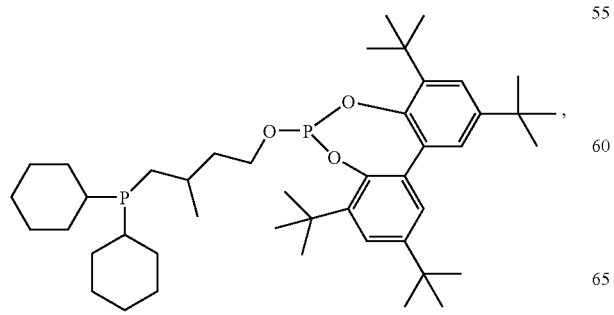

-continued (III)

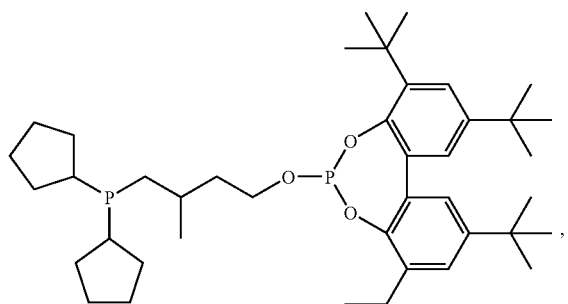

(V)

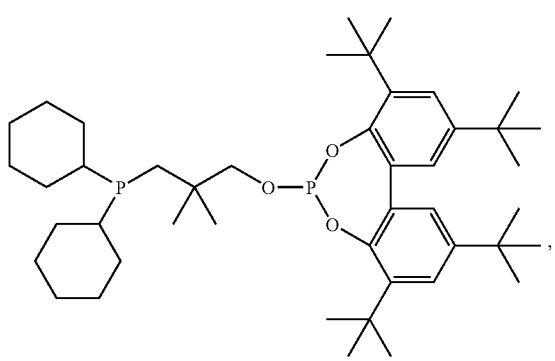

(VI)

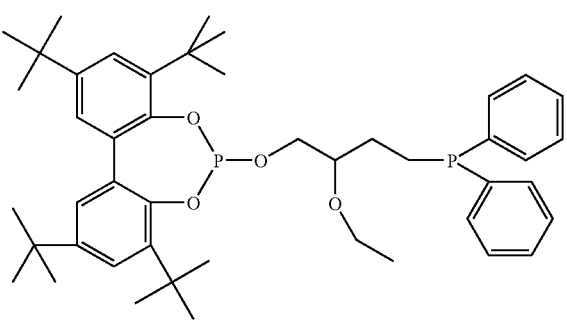

(VII)

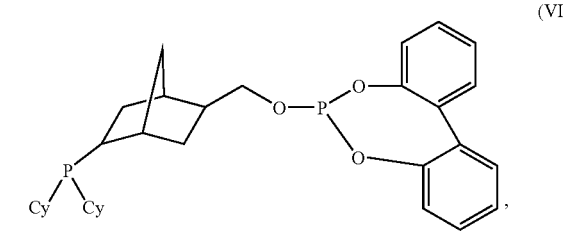

(VIII)

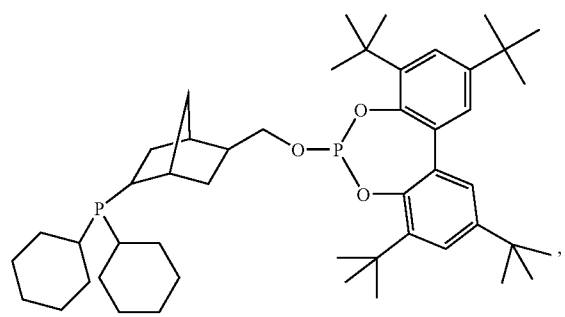

-continued
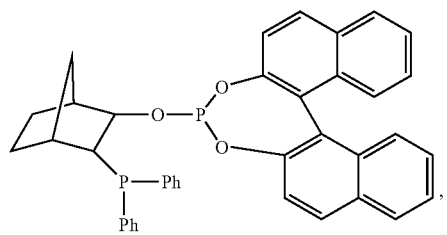 (IX)
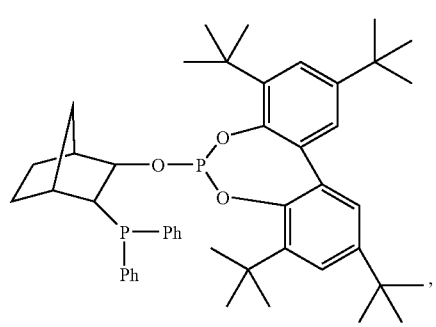 (X)
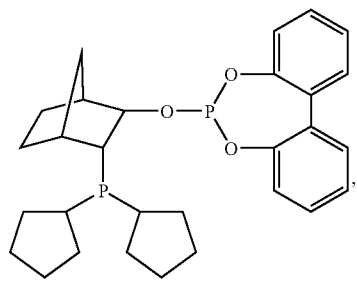 (XI)
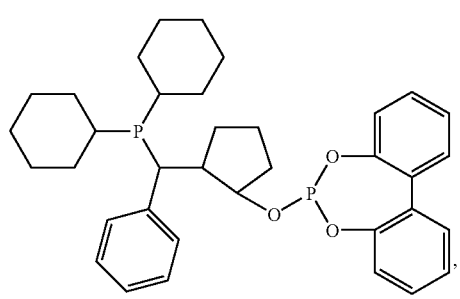 (XII)
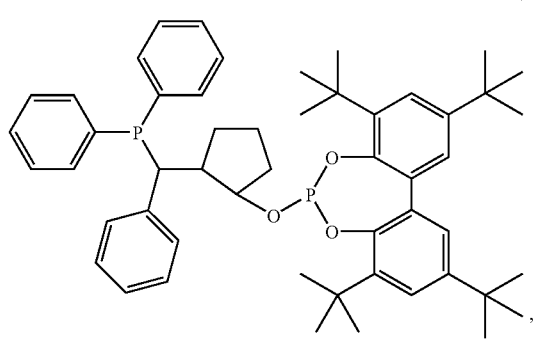 (XIII)
-continued
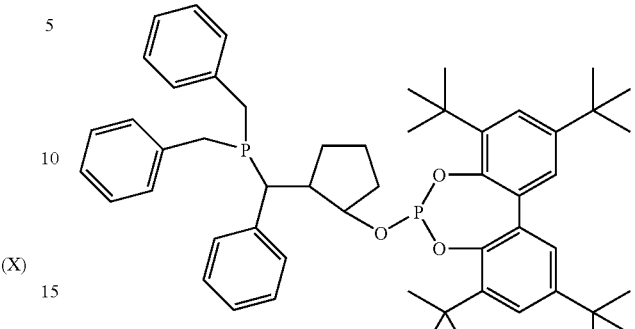 (XIV)
 (XV)
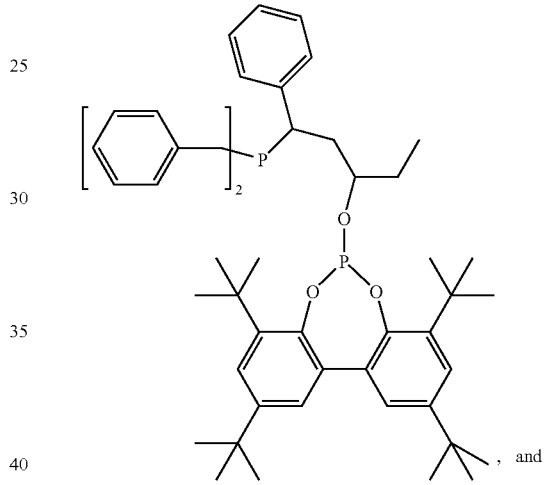, and
 (XVI)
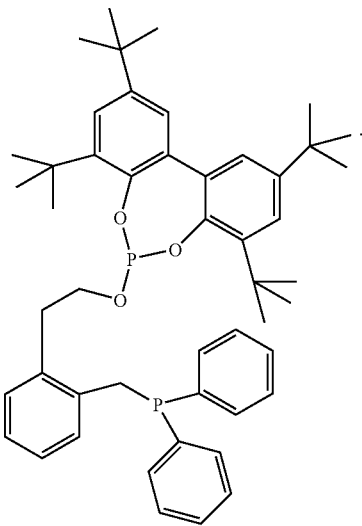

2. The compound according to claim 1, which has one of the following structures:
3. The compound according to claim 1, which has the following structure:
4. The compound according to claim 1, which has the following structure:
5. The compound according to claim 1, which has the following structure:
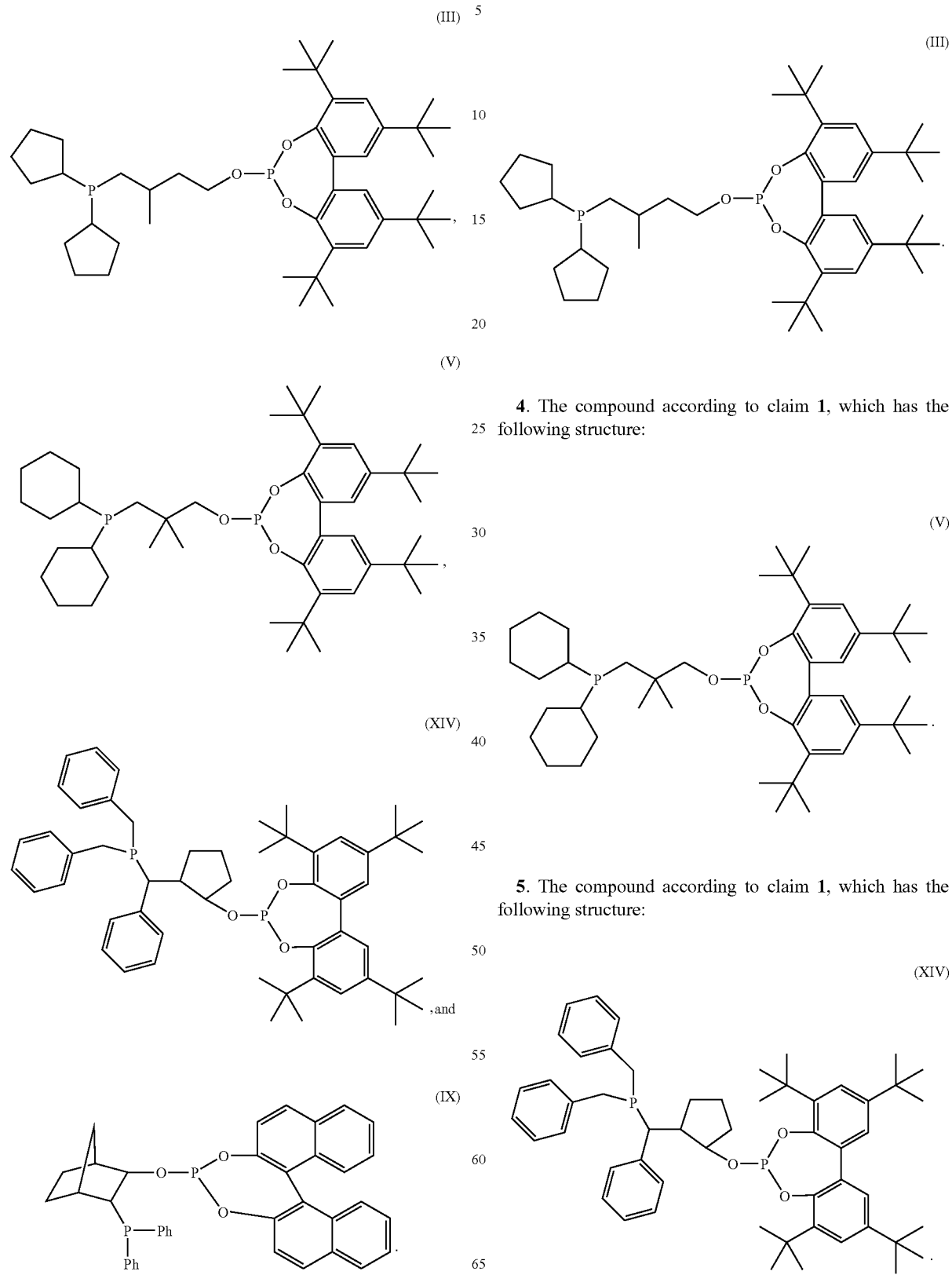

6. The compound according to claim 1, which has the following structure:
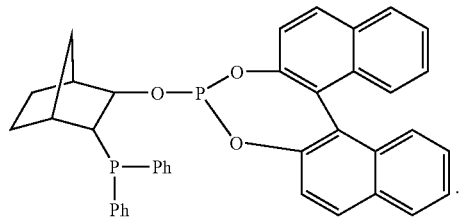
(IX)
7. A catalyst system comprising (A) at least one transition metal selected from rhenium and Group VIII metals and (B) at least one ligand selected from the following structures:
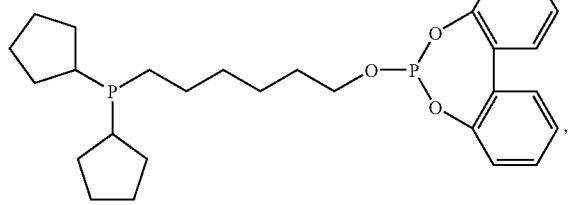
(I)
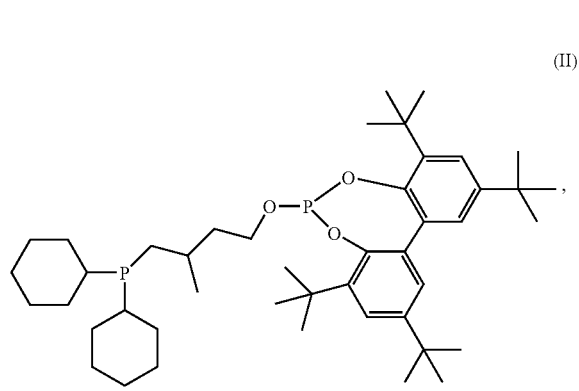
(II)
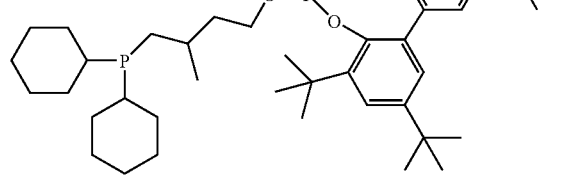
(III)
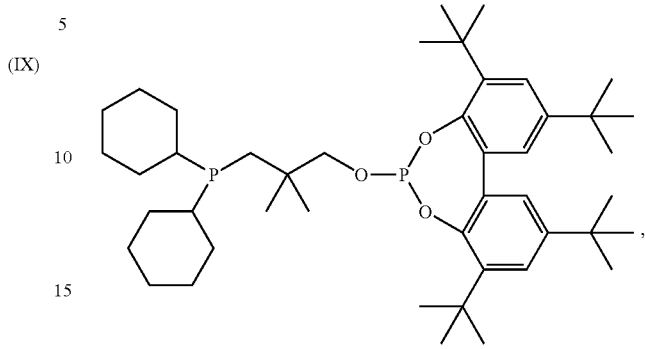
(V)
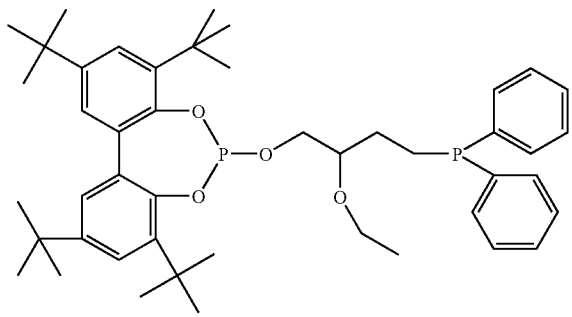
(VI)
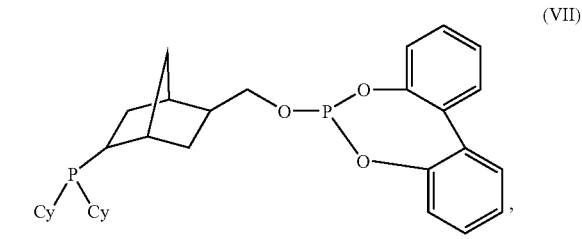
(VII)
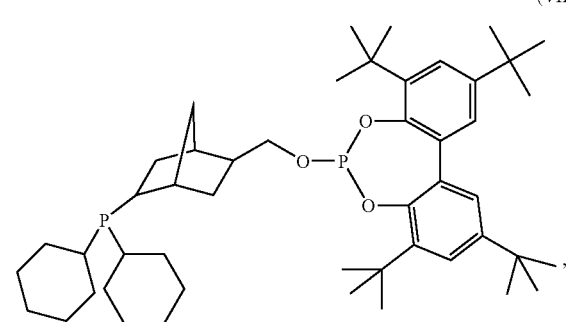
(VIII)
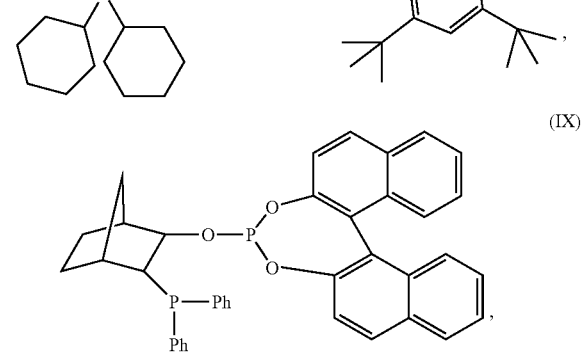
(IX)

-continued

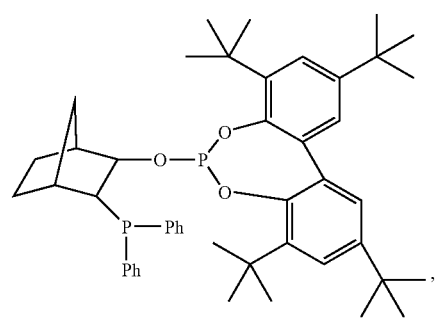
(X)

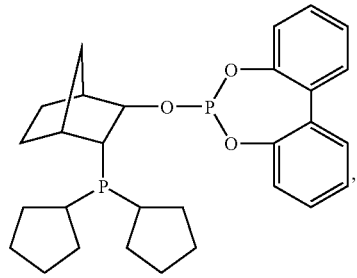
(XI)

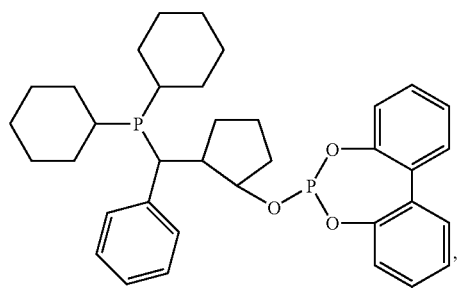
(XII)

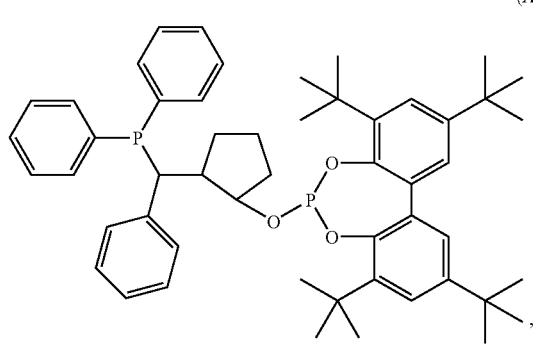
(XIII)

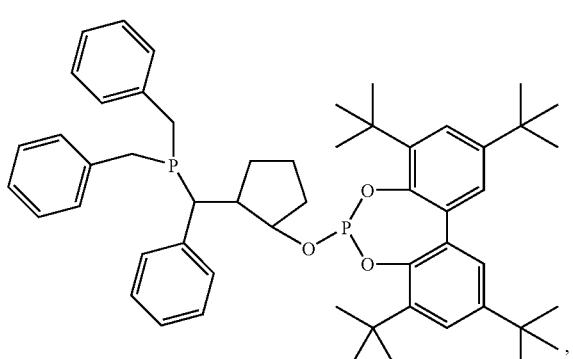
(XIV)

-continued

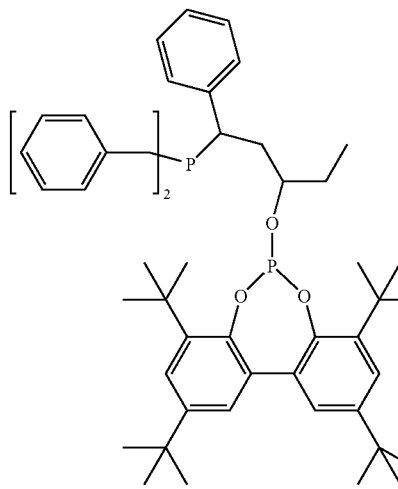
(XV)

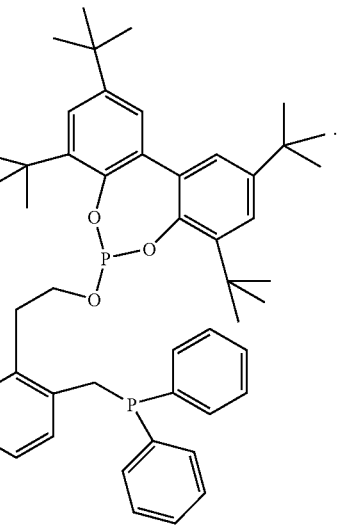
, and (XVI)

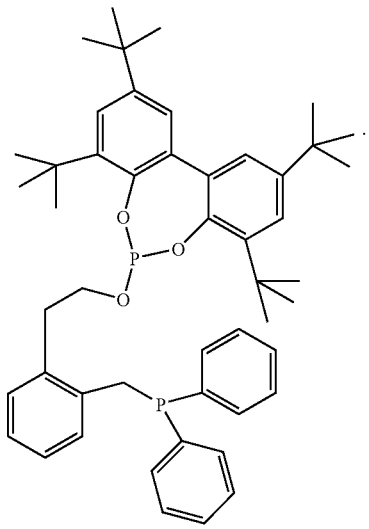

8. The catalyst system according to claim 7, wherein said metal is selected from rhodium, cobalt, nickel, ruthenium, iridium, palladium, and platinum.

9. The catalyst system according to claim 8, wherein said metal is rhodium.

10. The catalyst system according to claim 9, wherein said ligand is selected from the following structures:

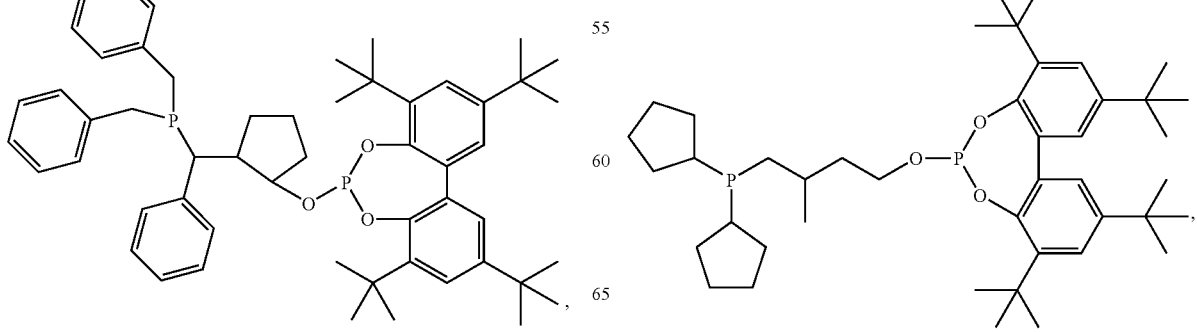
(III)

-continued

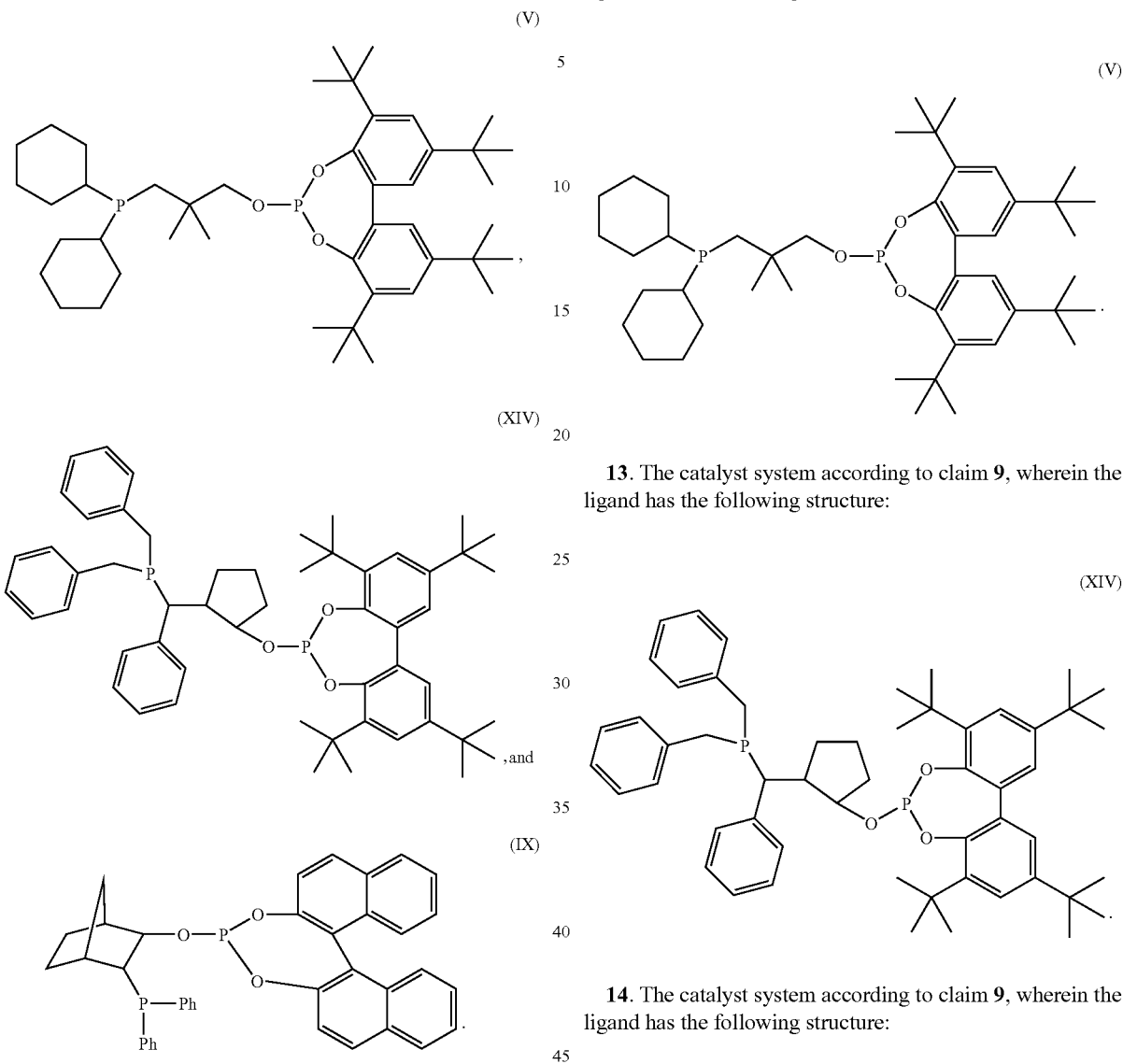

11. The catalyst system according to claim 9, wherein the ligand has the following structure:

12. The catalyst system according to claim 9, wherein the ligand has the following structure:

13. The catalyst system according to claim 9, wherein the ligand has the following structure:

14. The catalyst system according to claim 9, wherein the ligand has the following structure:

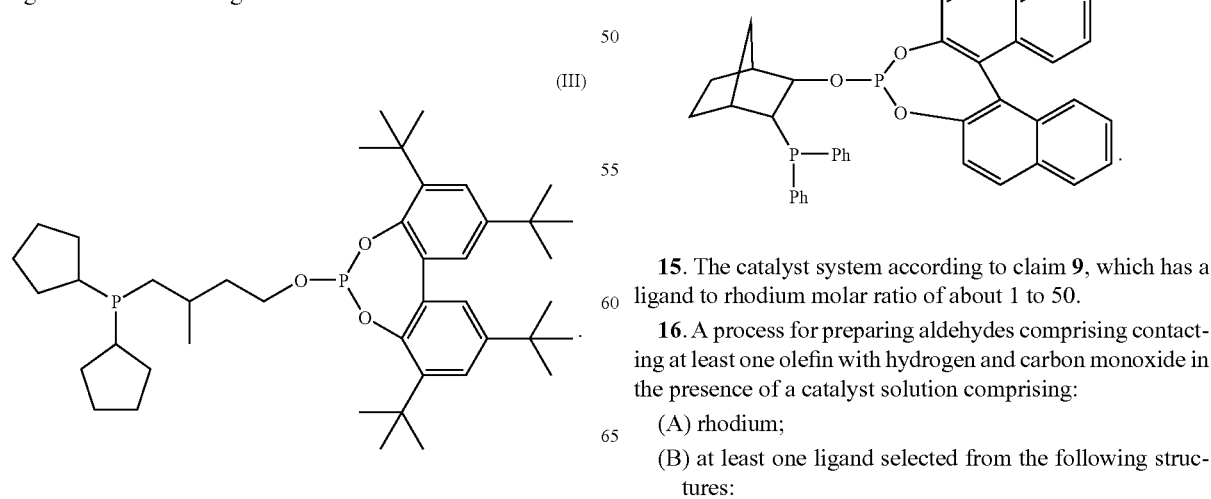

15. The catalyst system according to claim 9, which has a ligand to rhodium molar ratio of about 1 to 50.

16. A process for preparing aldehydes comprising contacting at least one olefin with hydrogen and carbon monoxide in the presence of a catalyst solution comprising:
 (A) rhodium;
 (B) at least one ligand selected from the following structures:

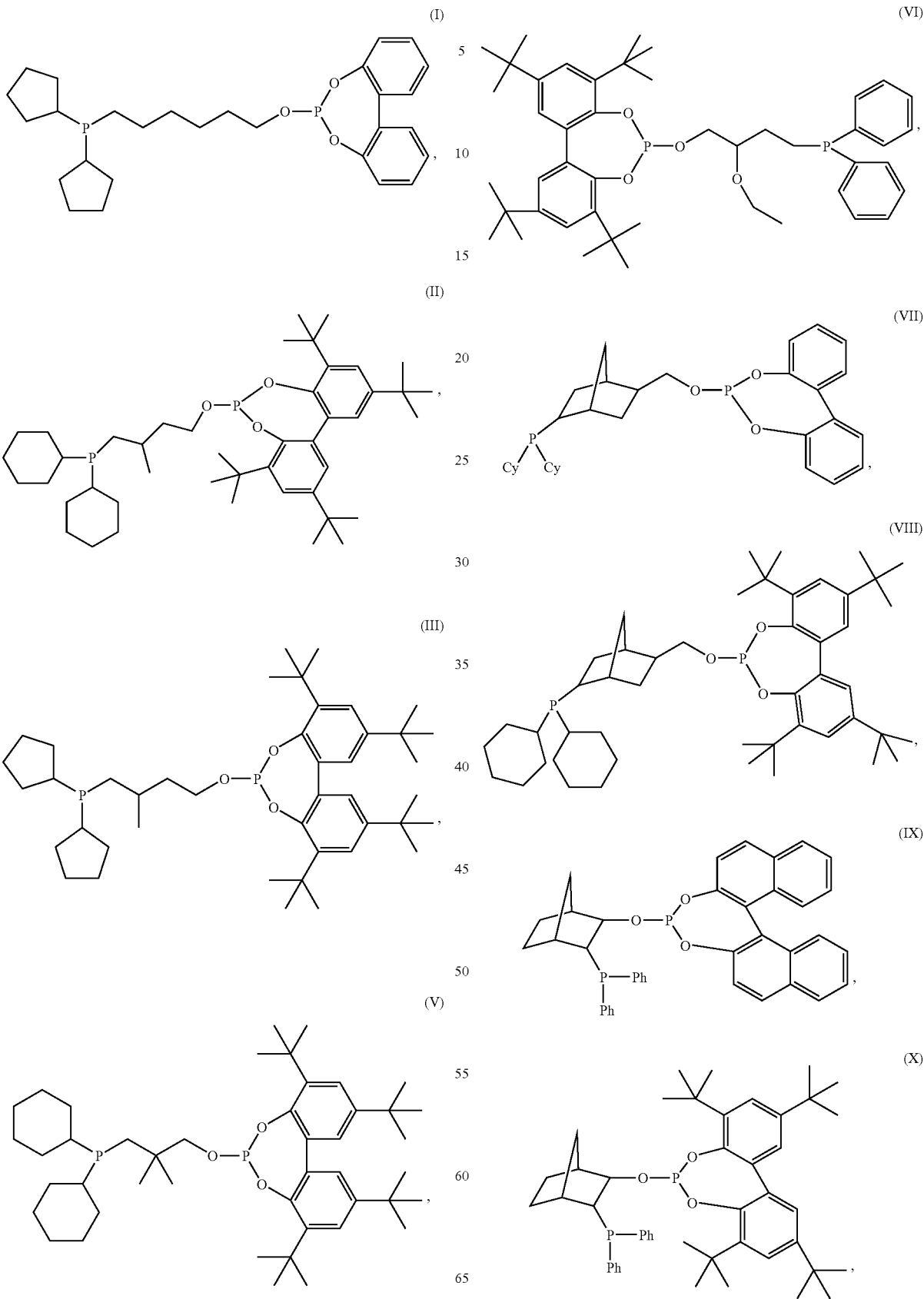

-continued
(XI)
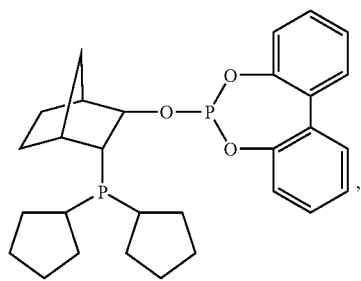
(XII)
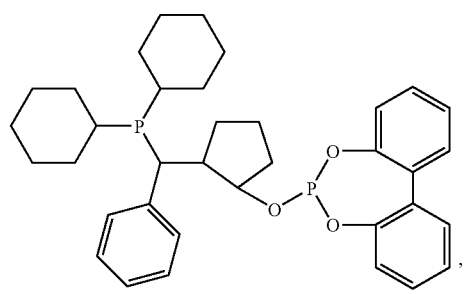
(XIII)
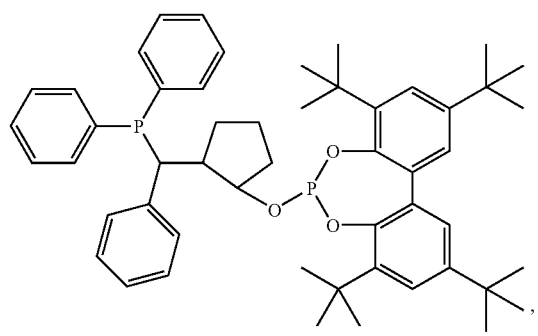
(XIV)
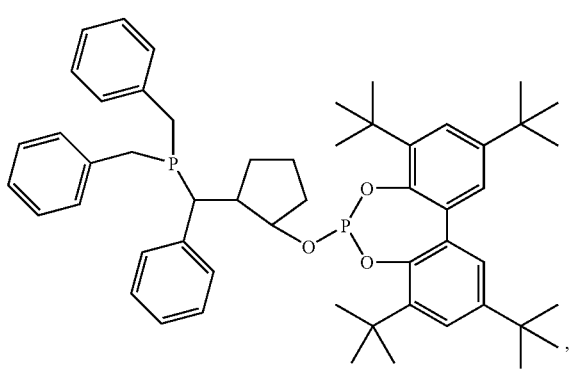
-continued
(XV)
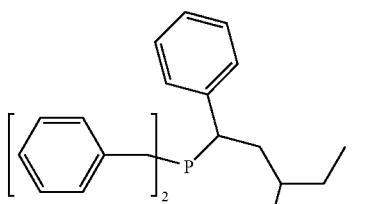
(XVI)
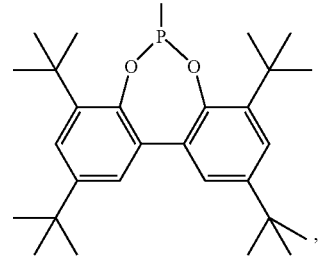
(C) a hydroformylation solvent.
17. The process according to claim 16, wherein said ligand is selected from the following structures:
(III)
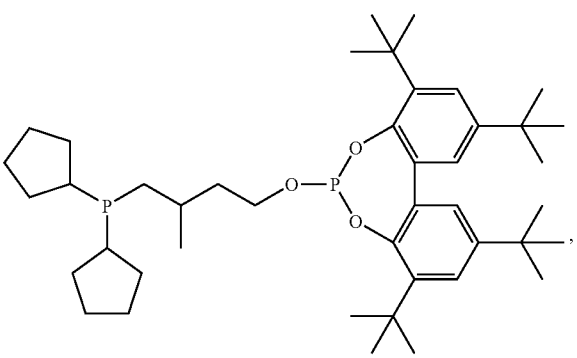

-continued

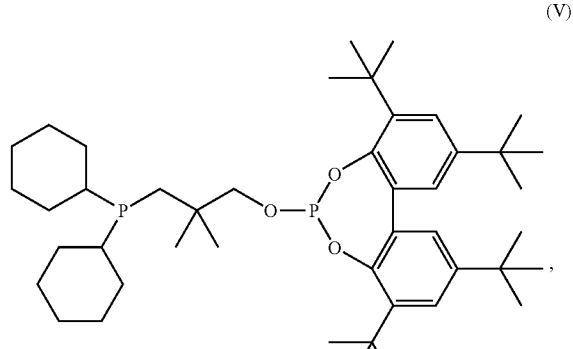

(V)

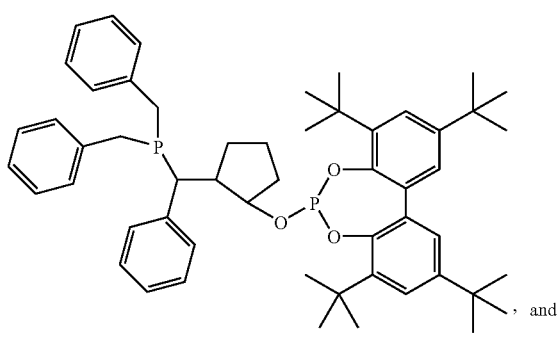

(XIV)

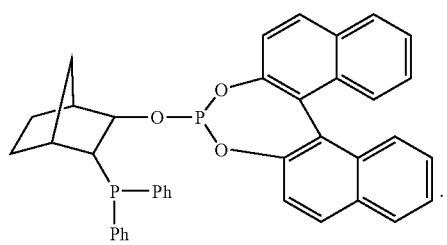

(IX)

18. The process according to claim 16, wherein said ligand has the following structure:

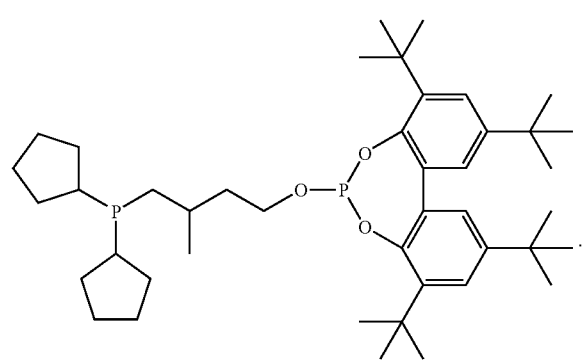

(III)

19. The process according to claim 16, wherein said ligand has the following structure:

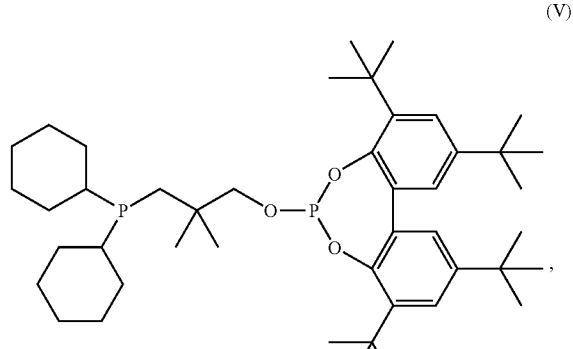

(V)

20. The process according to claim 16, wherein said ligand has the following structure:

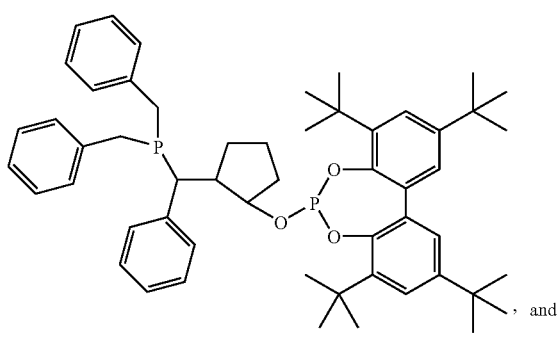

(XIV)

21. The process according to claim 16, wherein said ligand has the following structure:

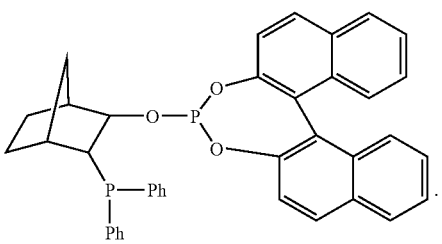

(IX)

22. The process according to claim 16, wherein said catalyst system has a ligand to rhodium molar ratio of about 1 to 50.

23. The process according to claim 16, wherein said contacting step is carried out at a pressure of 90 psig (621 kPa) to 450 psig (3103 kPa) and a temperature of 50° C. to 150° C.

24. The process according to claim 16, wherein the contacting step is carried out at a hydrogen partial pressure of about 20 psia (138 kPa) to 200 psia (1380 kPa), and a carbon monoxide partial pressure of about 20 psia (138 kPa) to 200 psia (1380 kPa).

25. The process according to claim 16, wherein said olefin is an optionally substituted, linear, branched, or cyclic, terminal or internal mono-olefin containing 2 to 20 carbon atoms, or an optionally substituted, non-conjugated polyolefin having 5 to 5,000 carbon atoms.

26. The process according to claim 16, wherein said olefin is propylene, isobutene, cis-2-butene, 1-hexene, 1-octene, 1-decene, allyl alcohol, allyl acetate, 4-hydroxy-1-butene, or 1,7-octadiene.

27. The process according to claim 16, wherein said hydroformylation solvent is selected from alkanes, cycloalkanes alkenes, cycloalkenes, carbocyclic aromatic compounds, esters, ketones, acetals, and ethers which are liquid at the pressure at which the process is being operated.

28. A method for changing the normal-to-iso product ratio of a process for preparing aldehydes, said method comprising:

(a) contacting an olefin with hydrogen and carbon monoxide, at a first hydrogen-to-carbon monoxide partial pressure ratio, in the presence of a catalyst solution comprising (A) rhodium; (B) at least one ligand selected from the following structures:

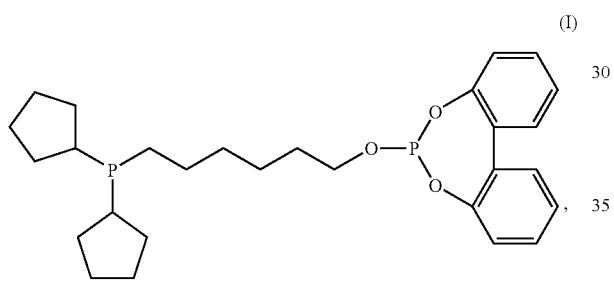
(I)

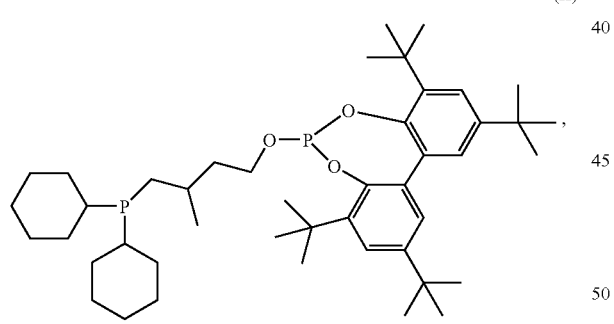
(II)

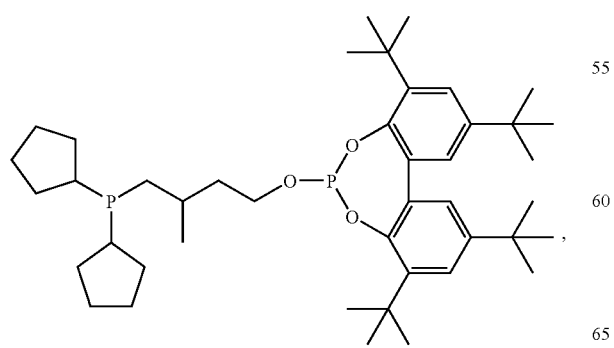
(III)

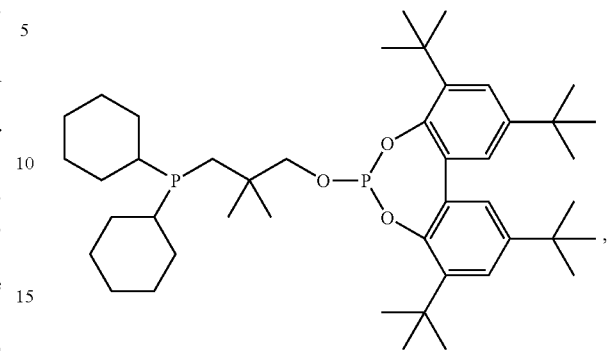
(V)

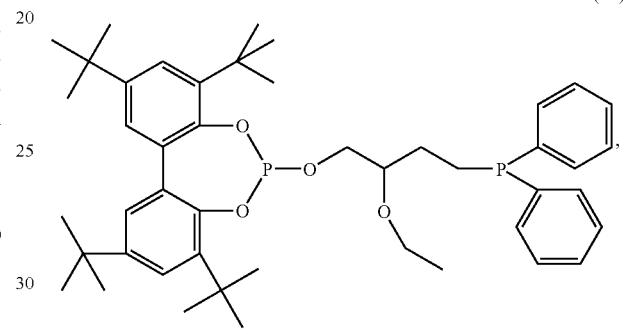
(VI)

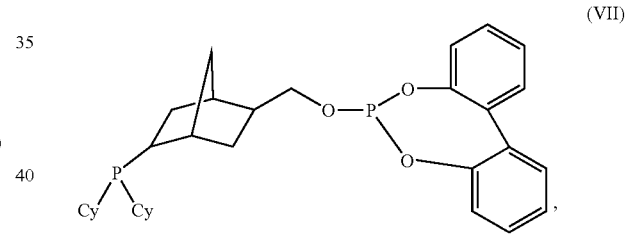
(VII)

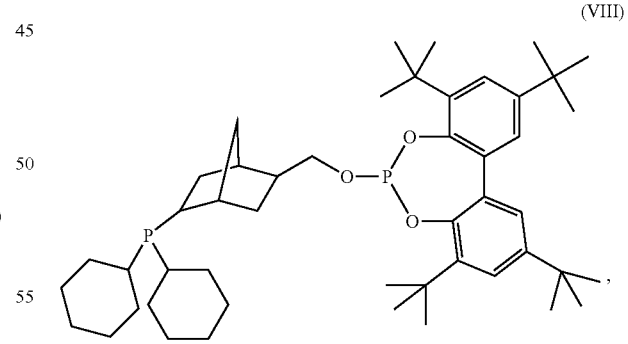
(VIII)

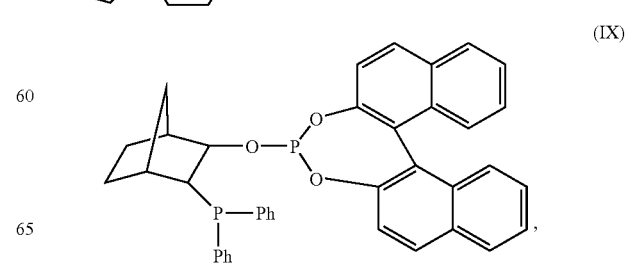
(IX)

-continued

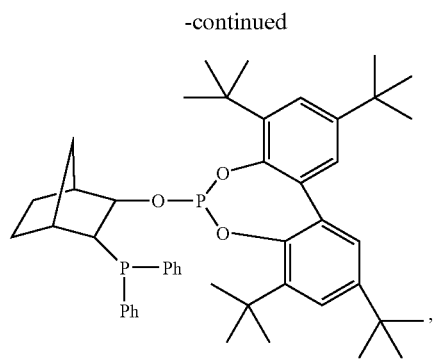
(X)

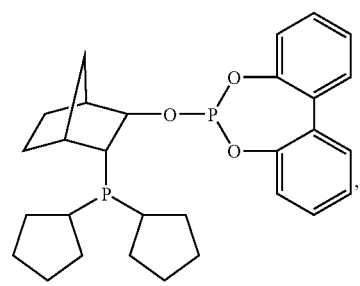
(XI)

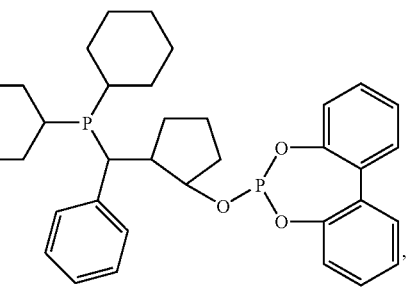
(XII)

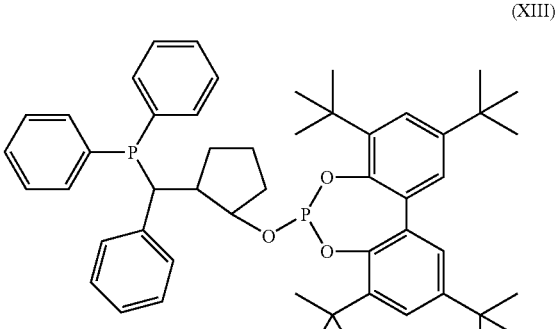
(XIII)

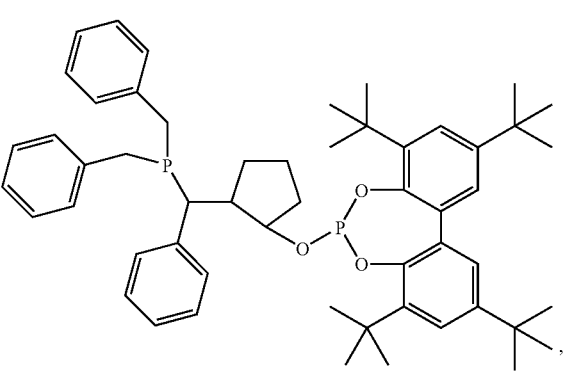
(XIV)

-continued

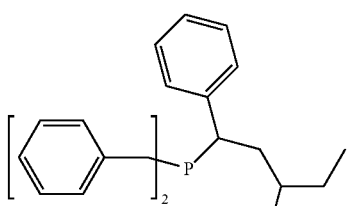
(XV)

, and

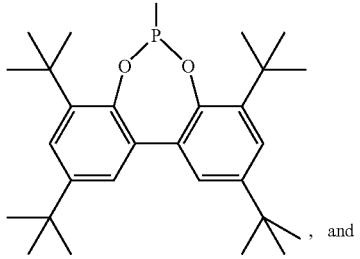
(XVI)

;

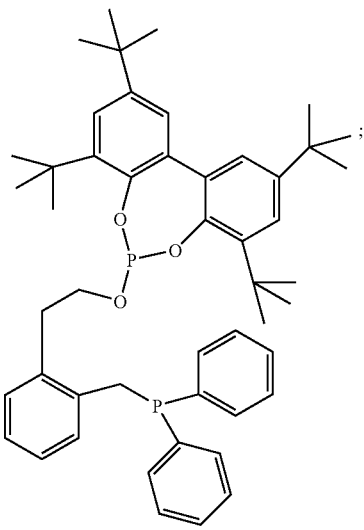

and (C) a hydroformylation solvent, to produce aldehydes having a first normal-to-iso product ratio; and (b) contacting said olefin with hydrogen and carbon monoxide, at a second hydrogen-to-carbon monoxide partial pressure ratio which is different from the first hydrogen-to-carbon monoxide partial pressure ratio, in the presence of said catalyst solution to produce aldehydes having a second normal-to-iso product ratio which is different from the first normal-to-iso product ratio.

29. The method according to claim 28, wherein said ligand is selected from the following structures:

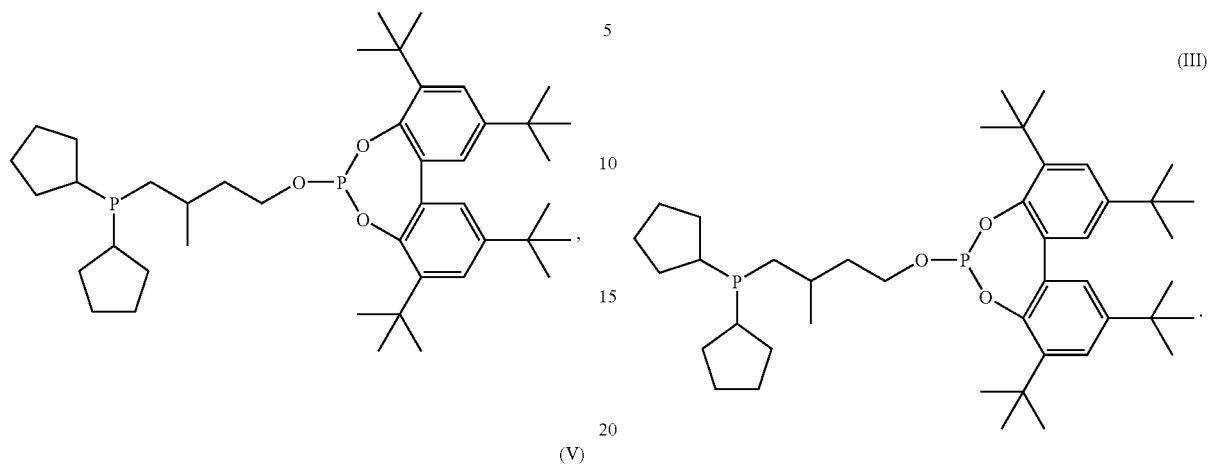
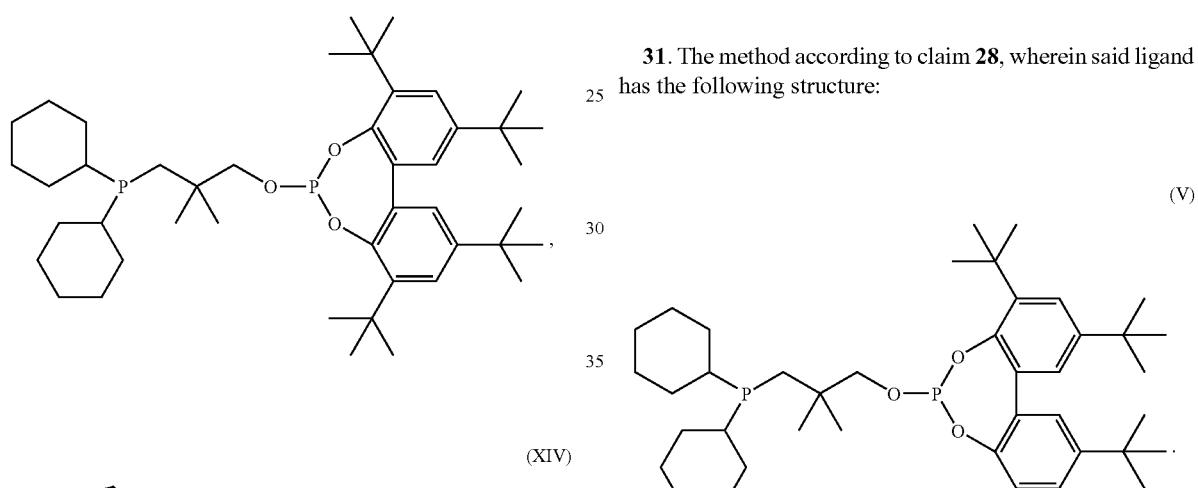
30. The method according to claim 28, wherein said ligand has the following structure:
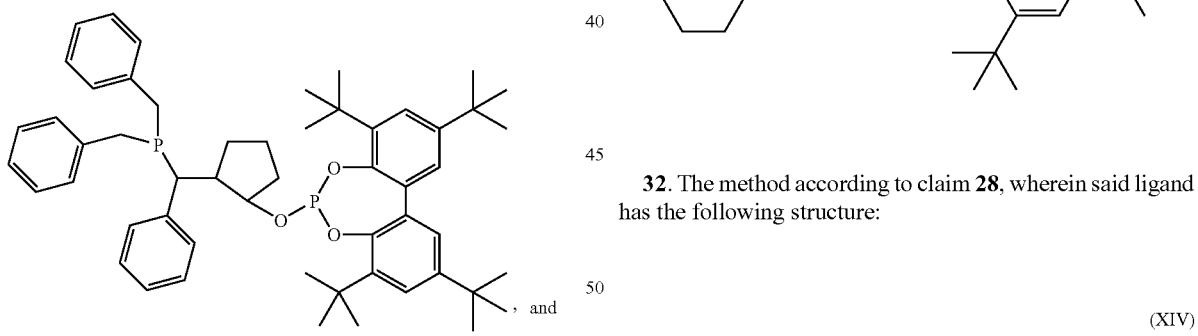
31. The method according to claim 28, wherein said ligand has the following structure:
32. The method according to claim 28, wherein said ligand has the following structure:
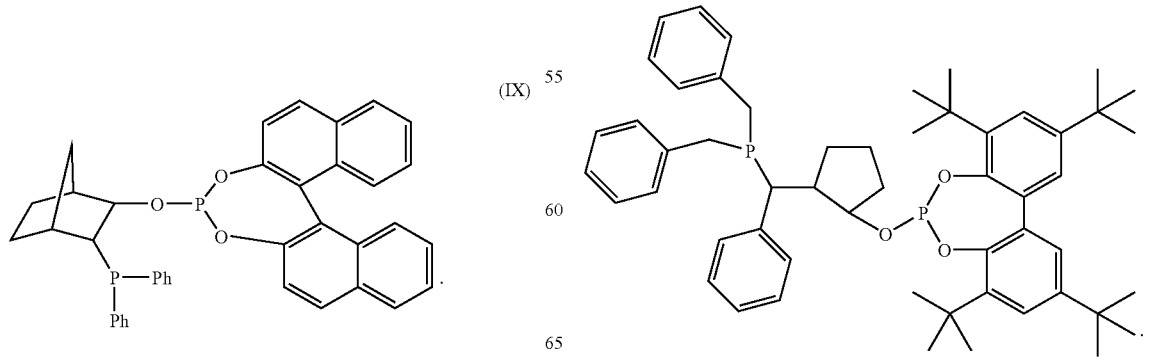

33. The method according to claim 28, wherein said ligand has the following structure:

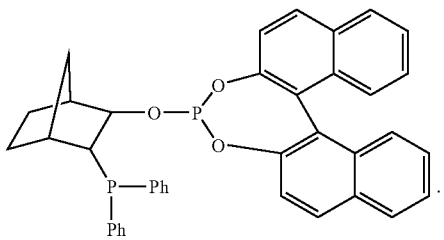

(IX)

34. The method according to claim 28, wherein said catalyst system has a ligand to rhodium molar ratio of about 1 to 50.

35. The method according to claim 28, wherein said contacting steps are carried out at a pressure of 90 psig (621 KPa) to 450 psig (3103 KPa) and a temperature of 50° C. to 150° C.

36. The method according to claim 28, wherein the contacting steps are carried out at a hydrogen partial pressure of about 20 psia (138 kPa) to 200 psia (1380 kPa), and a carbon monoxide partial pressure of about 20 psia (138 kPa) to 200 psia (1380 kPa).

37. The method according to claim 28, wherein said olefin is an optionally substituted, linear, branched, or cyclic, terminal or internal mono-olefin containing 2 to 20 carbon atoms; or an optionally substituted, non-conjugated polyolefin having 5 to 5,000 carbon atoms.

38. The method according to claim 28, wherein said olefin is propylene, isobutene, cis-2-butene, 1-hexene, 1-octene, 1-decene, allyl alcohol, allyl acetate, 4-hydroxy-1-butene, or 1,7-octadiene.

39. The method according to claim 28, wherein said hydroformylation solvent is selected from alkanes, cycloalkanes alkenes, cycloalkenes, carbocyclic aromatic compounds, esters, ketones, acetals, and ethers which are liquid at the pressure at which the process is being operated.

* * * * *